(12) United States Patent
Pilliar et al.

(10) Patent No.: US 7,494,614 B2
(45) Date of Patent: Feb. 24, 2009

(54) METHOD OF MANUFACTURE OF POROUS INORGANIC STRUCTURES

(76) Inventors: Robert M. Pilliar, 56 Rochester Avenue, Apartment 2104, Toronto (CA) M4N 1N8; Jenshong Hong, 35 Charles Strret West, Apartment 2104, Toronto (CA) M4Y 1R6; J. Paul Santerre, 83 Withburn Street, Whitby (CA) L1R 1R5

( * ) Notice: Subject to any disclaimer, the term of this patent is extended or adjusted under 35 U.S.C. 154(b) by 565 days.

(21) Appl. No.: 10/617,358

(22) Filed: Jul. 11, 2003

(65) Prior Publication Data

US 2004/0043051 A1     Mar. 4, 2004

Related U.S. Application Data

(60) Provisional application No. 60/395,273, filed on Jul. 12, 2002.

(51) Int. Cl.
     *B29C 65/00*      (2006.01)
(52) U.S. Cl. ....................................... 264/666; 623/901
(58) Field of Classification Search ................. 264/666, 264/109; 623/901, 16.11
See application file for complete search history.

(56) References Cited

U.S. PATENT DOCUMENTS 6,077,989 A     6/2000     Kandel (Continued)

FOREIGN PATENT DOCUMENTS

JP     3187987     8/1991
WO     0301016     11/2003

OTHER PUBLICATIONS

"Characterization of cartilagenous tissue formed on calcium polyphosphate substrates in vitro", Waldman et al., 2002 Wiley Periodicals, Inc., pp. 323-330.

(Continued)

*Primary Examiner*—Carlos Lopez
(74) *Attorney, Agent, or Firm*—Hill & Schumacher; Lynn Schumacher

(57) ABSTRACT

A sintering schedule to allow the reliable formation of inorganic or ceramic materials, exemplified using porous calcium polyphosphate samples to be used for forming novel implants for bone interfacing applications. The key to the successful definition of the process was the determination of the factors affecting the crystallization temperature of the powders that are gravity sintered to form porous samples of desired density and with a pore size range suitable for the particular application. The method involves applying a sintering procedure to a packed amorphous inorganic powder which gives control over densification and includes choosing sintering temperatures and times sequentially that correspond to the inorganic material being amorphous but having a viscosity to develop significant sinter necks between adjacent powder particles by a viscous flow sintering mechanism while maintaining a desired open-pored structure, followed by a second temperature at which crystallization of the packed amorphous inorganic powder occurs and during which slower diffusion-related mechanisms control sinter neck growth and densification to give a substantially crystalline porous, inorganic structure. In addition, interpenetrating phase composites of biodegradable organic polymers throughout the porous calcium polyphosphate samples were formed and resulted in the development of novel composites with attractive strength and toughness. These materials hold promise for formation of biodegradable fracture fixation implants and degradable anchoring systems for temporary stabilization of bone-interfacing implants designed for fixation by bone ingrowth.

43 Claims, 9 Drawing Sheets

U.S. PATENT DOCUMENTS 6,117,456 A    9/2000   Lee et al.
7,119,038 B2 * 10/2006  Lin et al. .................... 501/1

OTHER PUBLICATIONS

"Fabrication of porous calcium polyphosphate implants by solid freeform fabrication: A study of processing parameters and in vitro degradation characteristics", Porter et al., 2001 John Wiler & Sons, Inc., pp. 504-512.

"Porous calcium polyphosphate scaffolds for bone substitute applications—in vitro characterization", Pilliar et al., Biomaterials 22 (2001), pp. 963-972.

"Porous calcium polyphosphate scaffolds for bone substitute applications in vivo studies", Grynpas et al., Biomaterials 23 (2002) pp. 2063-2070.

"Condensed calcium phosphates for soft tissue and bone repair/regeneration", Filiaggi et al., Bioceramics, vol. 11, pp. 341-344, 1998.

"Porous-surfaced metallic implants for orthopedic applications", Pilliar, Journal of Biomedical Materials Research, vol. 21, No. A1, pp. 1-33, 1987.

"On the sintering characteristics of calcium polyphosphates", Filiagge et al., Key Engineering Materials, vols. 192-195 (2001), pp. 171-174.

* cited by examiner a                                    b

METHOD OF MANUFACTURE OF POROUS INORGANIC STRUCTURES

CROSS REFERENCE TO RELATED U.S APPLICATIONS

This patent application relates to, and claims the priority benefit from, U.S. Provisional Patent Application Ser. No. 60/395,273 filed on Jul. 12, 2002, which is incorporated herein by reference in its entirety.

FIELD OF INVENTION

The present invention relates to porous inorganic (ceramic) structures in monolith form or for use as a porous structure for infiltration with an appropriate organic polymer to form novel interpenetrating phase ceramic/polymer composites, and in particular a method of manufacturing such structures.

BACKGROUND OF THE INVENTION

The pursuit of new composite materials is driven in part by the need for materials which exhibit combined selected properties of the constituent components making up the composite. A very useful class of inorganic materials is the ceramics, examples being metal oxides and metal phosphates or any other inorganic (ceramic or glass) material characterized by ionic and/or covalent interatomic bonding and typically displaying brittle fracture with stresses exceeding the fracture strength.

Typically, ceramics are able to resist compressive forces very well but not tensile or shear forces. This limits the usefulness of ceramics for many load-bearing applications as well as methods for forming to final shape thus presenting a major drawback for using this material for many applications for which the ceramic would otherwise be very suitable or desirable. However, many ceramics can provide high stiffness to structures by virtue of their high elastic modulus and they can also provide good wear resistance. Their brittle behaviour is related to the inability to plastically deform resulting in easy crack initiation at surface or internal flaws and defects introduced either during material formation or fabrication of components. Cutting or grinding operations can introduce micro-cracks within ceramic parts that can act as additional critical stress concentrators promoting easy unstable crack propagation.

By comparison, polymers are relatively compliant and characterized by a low elastic modulus and the ability to deform significantly prior to failure typical of polymeric materials and so it would be useful to be able to produce a composite material that combines the hardness and high modulus of ceramics with the deformability of polymers thereby creating novel materials with enhanced energy absorption capability and fracture resistance. For example, there are many applications for light-weight energy absorbing structures such as crash resistant barriers, bullet- or explosion-proof protective gear and fracture resistant ceramic-based structural materials. Also, formation of such materials would allow certain machining or shaping procedures that cannot be applied to conventional ceramics because of their intrinsic brittleness and inability to tolerate defects introduced during machining and shaping.

Formation of new ceramic-based materials able to resist easy crack initiation and propagation would potentially provide materials with the benefits of ceramics (hardness, wear resistance, higher stiffness than organic polymers) that could be used reliably in certain load-bearing applications. Such materials would be less susceptible to fracture as a result of unintended mishandling, unexpected loading, or microdamage introduced through machining and forming operations.

Currently, strategies for forming tougher ceramics include introducing crack arrestors (boundaries between different phases or lamellae that can de-bond during crack propagation causing crack deflection), or promoting residual compressive stresses in the materials through selection and combination of materials with appropriate thermal expansion coefficients, or through 'alloying' to retain metastable phases that can transform during loading thereby creating zones of residual compression at crack tips (transformation induced toughening), or through substitution of larger ions into the crystal lattice of the ceramic to cause residual compressive stresses. None of these approaches focuses on reducing local stress concentrations that can result in crack initiation by re-distributing stresses through a well-bonded, compliant organic phase.

Combining a porous inorganic ceramic with an appropriate infiltrating polymer to form an interpenetrating phase composite, offers a novel strategy for improving the toughness and strength of ceramic-based composites. The combination of ceramic and organic polymer also makes possible a very low density final composite thereby providing superior specific strength and toughness properties (i.e. strength and toughness per weight).

A particular field using ceramics based on calcium polyphosphates is biomedical or dental applications that require biodegradable structures for implants and the like. Calcium polyphosphates (CPP) are inorganic polymers $[Ca(PO_3)_2]_n$ consisting of networks of oxygen-bridged $(PO_4)^{3-}$ tetradedra and shared $Ca^{2+}$ ions (one per pair of phosphate tetrahedra). Studies by the inventors have shown that porous structures made of CPP are biodegradable and, as such, offer potential for a number of novel biomaterial applications including use as substrates for forming tissue-engineered implants for the repair and augmentation of degraded soft and hard tissues and, in particular, for anchoring soft connective tissues to bone (e.g. cartilage or ligament to bone) [Filiaggi M J et al, Bioceramics 11:341-344, 1998; Pilliar R M et al, Biomaterials 22:963-972, 2001; Grynpas M D et al, Biomaterials, 23:2063-2070, 2002; Waldman S et al, J Biomed Mater Res., 62:323-330, 2002]. Porous CPP substrates of desired structure can be formed by sintering CPP powders of appropriate size.

Cell culture methods can then be used to form tissues such as articular cartilage firmly anchored to the porous CPP (through mechanical interdigitation of the in vitro-formed cartilage with the porous CPP structure). The porous CPP also allows bone ingrowth throughout its open-pored structure following implantation in vivo thereby providing a means for securely anchoring articular cartilage or other soft connective tissues (e.g. ligament, tendon, fibrocartilage) to bone. Articular cartilage-CPP 'plugs' so formed potentially represent a novel approach for the repair of focal cartilage defects that, if left untreated, may progressively increase in size leading eventually to the need for total joint replacement surgery using traditional implants made of metals, polymers, or ceramics. It is recognized that this traditional approach has a finite lifetime (approximately 15 years for normally active individuals). The consequences for treatment of younger individuals (those less than 55 years old) is that revision surgery represents an inevitable consequence following primary placement of conventional joint replacement implants as used today assuming patient survival.

Therefore it would be very advantageous to develop an alternative treatment approach involving the use of tissue-engineered implant systems for early-stage replacement of identified focal cartilage defects using porous CPP structures as substrates on which suitable tissues can be grown and anchored in vitro prior to implantation of the tissue-CPP 'plug' into an identified defect site. In this manner, the defective region of cartilage and underlying subchondral bone (which may or may not be degraded) is replaced by newly-formed healthy tissues. With time the biodegradable CPP component will degrade, being replaced wholly by bone and the overlying articular cartilage surface layer. The porous CPP construct serves as a temporary template for both in vitro and in vivo tissue formation (e.g. cartilage and bone). Our ongoing animal studies have demonstrated the ability to repair osteochondral defects by this method. The results of these studies using sheep (knee joint defects) have been encouraging in our initial short-term (3 month) experiments. Longer-term studies of in vivo degradation rates of the porous CPP constructs placed in rabbit femoral condyle sites have been reported [Grynpas M D et al, Biomaterials, in press, 2002]. Future studies are planned to investigate the response over the longer-term of osteochondral defect repair 'plugs'.

A key to the development of these novel biphasic (i.e. CPP+cartilage tissue) 'plugs' is the formation of a suitable porous CPP substrate. It is therefore important to develop methods for reliably forming porous CPP structures of desired strength and architecture. It is known that an interconnected porous network with an average pore size in the range of 50 to 100 microns will allow rapid bone ingrowth provided that the materials forming the porous structure are biocompatible and suitable initial stability is maintained during early healing [Pilliar R M, J Biomed Mater Res., 21:1-33, 1987]. It is critical that the porous CPP 'plugs' exhibit sufficient strength to allow handling including an ability to be forcefully press-fitted into a prepared site (necessary for achieving the required initial stability) as well as being able to withstand any imposed forces due to normal activities preceding extensive bone ingrowth. Previous studies have indicated that an initial porosity corresponding to about ~35 volume percent of appropriate pore size range (~50 to 100 µm) appears suitable for both securely anchoring articular cartilage during its in vitro formation and allowing rapid bone ingrowth in vivo.

Therefore, it is necessary to be able to reproducibly achieve the desired open-pored structure while maintaining reasonable mechanical strength of the porous CPP. Due to the inorganic nature of CPP, this presents a challenge since porous ceramic structures in general have low fracture resistance, particularly under complex loading conditions involving tension and shear. Some of the inventors have previously experienced some success in forming suitable porous CPP constructs and had progressed to the point of demonstrating the feasibility of in vitro tissue formation and anchorage to a porous CPP substrate as proposed. This resulted in a U.S. Provisional patent application that was submitted in May 1998 followed subsequently by a full filing and a U.S. patent being granted in June 2000 as U.S. Pat. No. 6,077,989. However, during the course of these early studies, difficulties were encountered in reproducibly forming components of acceptable strength and structure. Thus, development of a method of processing CPP ceramics including the sintering conditions required to achieve reproducible structures reliably is a necessary condition to develop this alternative treatment approach. Such a method would be very useful in general to processing of any ceramic material that have the requisite properties to be processed in a similar way to CPP.

In addition to being able to reproducibly produce ceramics with desired porosity and connectivity of the pores, as mentioned above, it would be very advantageous to provide a method for increasing the mechanical strength and reducing the brittleness of ceramics. Previous studies in 1998 [Cipera E, MASc Thesis, University of Toronto, 1998] have shown that infusing porous CPP structures with a known biodegradable polymer (polycaprolactone (PCL)) resulted in significant increases in the energy to fracture compared with uninfiltrated porous CPP. However, the properties of the organic phase (polycaprolactone) were not considered ideal both in terms of its degradation rate and its ability to wet the CPP phase. Thus a different approach is required in order to develop novel biodegradable composite structures consisting of interpenetrating inorganic (CPP) and organic polymeric phases, both components being biodegradable at appropriate rates that confer greater mechanical strength to the ceramic phase. Such interpenetrating phase composites (IPC) would be useful for fabricating implants for use in assisting bone fracture repair (e.g. fracture fixation plates, intramedullary rods, screws, pins).

SUMMARY OF THE INVENTION

An objective of the present invention is to provide a method for producing an open-pored structure in ceramic materials. The method involves using a sintering procedure that allows control of the degree of densification during sintering through initial rapid sinter neck development by a viscous flow sintering mechanism followed by crystallization resulting in significant slowing of the rate of sinter neck growth and sample densification. This is achieved by choosing sintering temperatures and times sequentially that correspond to a temperature and time at which the inorganic material is amorphous but displays relatively low viscosity followed by a temperature above the crystallization temperature during which slower diffusion-related mechanisms control sinter neck growth and densification, or achieving the two conditions by continuous heating from a low temperature to above the crystallization temperature at an appropriate rate to achieve the same structures.

A particular ceramic suitable for use in biomedical applications that can be processed in this manner to give desired porous structures useful in biodegradable/resorbable implant development is calcium polyphosphate (CPP) and thus an objective of the present invention is to provide a method for producing an open-pored structure with CPP.

Another objective of the present invention is to provide new composite materials based on ceramics interpenetrated with polymers in order to form more fracture resistant ceramic-based materials.

The present invention provides a method for producing porous ceramic materials that allows control over pore size and connectivity of the pores. In addition to the formation of biodegradable biomaterial structures based on porous CPP as described above, other non-biodegradable structures suitable for use in medical or dental applications or for any other general application including the formation of interpenetrating phase composites as described below and displaying certain advantages as a result of either their method of fabrication or resulting properties are possible provided that the materials used in their fabrication display certain characteristics. These characteristics include: glass transition temperature and glass softening temperature<crystallization (devitrification) temperature<melt temperature, for the inorganic materials.

The present method also provides new ceramic/polymer composites by combining ceramics produced with controlled pore size and pore connectivity (either using the novel process referred to above or other more conventional process for forming porous ceramic structures) with polymers which can form strong primary chemical interatomic bonds (ionic or covalent) between the polymer and the porous, inorganic ceramic or glass material. The polymers should also exhibit low viscosity and good flowability coupled with possible heat- or light-activated polymerization in situ after infiltration into the pores of the inorganic structure, and have the ability to wet and form a strong primary bond with the inorganic phase.

Particular composite materials produced from an inorganic (ceramic) material and a polymer are biodegradable composite structures comprised of interpenetrating inorganic calcium polyphosphate(CPP) ceramics and organic polymeric phases, both components being biodegradable at appropriate rates. Such interpenetrating phase composites (IPC) may be useful for fabricating implants for use in assisting bone fracture repair (e.g. fracture fixation plates, intramedullary rods, screws, pins).

Examples of other applications for the composite ceramic/polymer materials produced in accordance with the present invention are non-biodegradable/resorbable composites to form crowns and jackets for tooth restoration in dentistry that can readily be formed to a desired shape by grinding or otherwise shaping at the patient's chair-side, and light-weight energy absorbing structures such as crash resistant barriers, bullet- or explosion-proof protective gear, fracture resistant ceramic-based building materials to mention just a few.

In another aspect of the invention there is provided a method for forming an inorganic material into three dimensional structures, comprising the steps of:
  a) forming an amorphous inorganic powder material, having a melting temperature, a crystallization temperature, a glass transition temperature and a glass softening temperature;
  b) packing the formed amorphous inorganic powder material to produce packed amorphous inorganic powder;
  c) pre-sintering the packed amorphous inorganic powder by heating said powder to a temperature greater than the glass transition temperature and the glass softening temperature and less than the crystallization temperature and holding steady at said temperature for an appropriate period of time greater to produce a pre-sintered amorphous inorganic body; and
  d) annealing the pre-sintered amorphous inorganic body to a final sintering temperature above the crystallization temperature and below the melting temperature to form a three dimensional porous crystalline inorganic structure.

In another aspect of the invention there is provided a method for forming a three dimensional porous crystalline inorganic structure, comprising the steps of:

method for forming a three dimensional porous crystalline inorganic structure, comprising the steps of:
  a) forming an amorphous inorganic powder material having a melting temperature, a crystallization temperature, a glass transition temperature and a glass softening temperature;
  b) packing the formed amorphous inorganic powder material to produce a packed amorphous inorganic powder;
  c) mixing fine powder particles of the amorphous inorganic powder material with a fluid carrier, and immersing the packed amorphous inorganic powder in the fluid carrier which has been mixed with the fine powder particles of the amorphous inorganic powder material to allow the fine powder particles to be distributed throughout the pores and on the surface of the packed amorphous inorganic powder following evaporation of the fluid carrier;
  d) pre-sintering the packed amorphous inorganic powder with the fine powder particles distributed therethrough at a pre-sintering temperature which is above the glass softening and the glass transition temperature but sufficiently low and for a short enough period of time to prevent the crystallization of the fine powder particles but to bond the fine powder particles to the packed amorphous inorganic powder; and
  e) annealing the pre-sintered packed amorphous inorganic powder to a final sintering temperature above the crystallization temperature and below the melting temperature to form a three dimensional porous crystalline inorganic structure.

BRIEF DESCRIPTION OF THE DRAWINGS

The invention will now be described, by way of example only, with reference to the accompanying drawings, in which.

DETAILED DESCRIPTION OF THE INVENTION

Definitions

Figure 1:
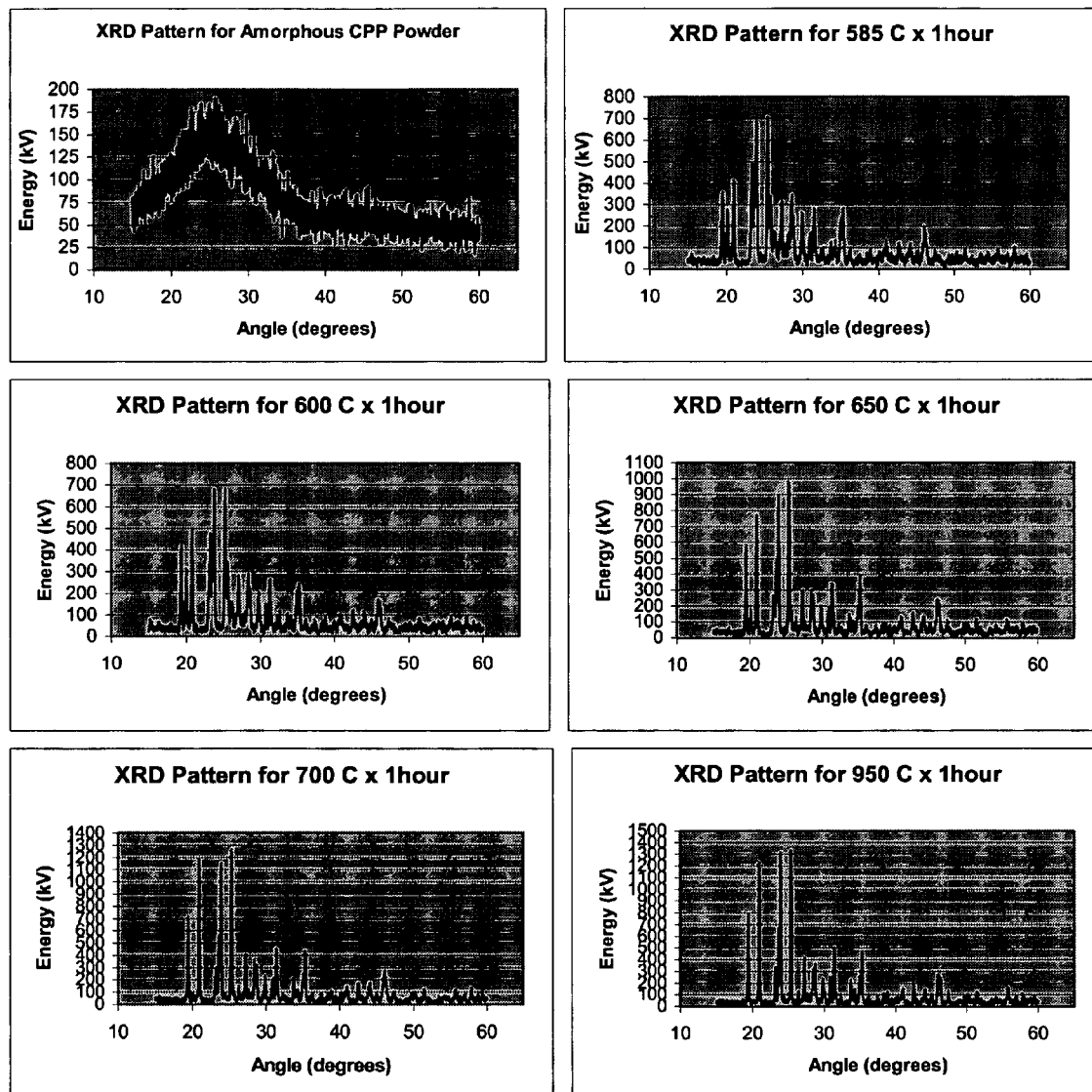
FIG. 1 shows X-ray Diffraction (XRD) spectra of amorphous CPP powders and samples sintered at different temperatures (585-950° C.)

As used herein, the term "inorganic powder material" means a powder of an inorganic or ceramic material such as for example calcium polyphosphate or $Al_2O_3$ or $ZrO_2$ or variants of these including other additives such as partially stabilized zirconia (PSZ), or any other inorganic (ceramic or glass) material characterized by ionic and/or covalent interatomic bonding and typically displaying brittle fracture with loads exceeding the fracture strength.

As used herein, the term "melting temperature" means the temperature at which a solid phase transforms to its liquid phase.

As used herein, the term "crystallization temperature" means the temperature above which an amorphous material transforms to a material with a well-defined crystalline structure. This may be strongly or weakly dependent on hold time at a specific temperature.

As used herein, the term "glass transition temperature" means the temperature at, and above which, an inorganic material begins to display significant viscous flow. It is the temperature at which an inorganic (or organic) polymer becomes more easily deformed as a result of the breakdown of interatomic covalent and/or ionic bonds.

As used herein, the term "glass softening temperature" means the temperature at, and above which, an inorganic amorphous ceramic or glass displays significant viscous flow.

As used herein, the phrase (or similar phrases) "a polymer being able to form strong primary chemical interatomic bonds (ionic or covalent) with the porous, inorganic ceramic material" means broadly an organic polymer which can form strong ionic or covalent bonds with the ceramic or glass surface that it contacts, and more preferably it means an organic polymer with positively- or negatively-charged side groups that will form a strong ionic bond with the ceramic or glass surface that it contacts. The invention disclosed herein provides a new method of producing an open-pored structure in ceramic materials. The inventors have discovered a sintering procedure that allows control of the degree of densification during sintering through initial rapid sinter neck development by a viscous flow sintering mechanism followed by crystallization resulting in significant slowing of the rate of sinter neck growth and sample densification. This can be achieved by choosing sintering temperatures and times sequentially that correspond to a temperature and time at which the inorganic material is amorphous but displays viscous flow followed by a temperature above the crystallization temperature during which slower diffusion-related mechanisms control sinter neck growth and densification, or achieving the two conditions by continuous heating from a low temperature to above the crystallization temperature at an appropriate rate to achieve the same structures.

The results of studies allowing the methodology of this new process as applied specifically to calcium polyphosphate (CPP) will be first disclosed herebelow followed by the generalization of this new process to other ceramics in general. With respect to CPP the determination by the inventors of the mechanism acting during sinter neck formation of sintered CPP powders and the effects of relative humidity on this has resulted in the design of sintering schedules for reliable formation of porous CPP parts. As a result both monolithic porous CPP components to be used for forming tissue-engineered implants (particularly ones involving soft tissue-to-bone attachment) are possible as well as the use of such porous structures to be used for infiltration with appropriate organics that can polymerize subsequently in situ to form novel interpenetrating phase composites. Following the results of these studies the new interpenetrating phase composites made of inorganic-organic constituents and their method of synthesis will be discussed, with non-limiting examples related to CPP being presented for illustrative purposes only.

Monolithic Porous CPP Structures—Sintering Studies

Amorphous calcium polyphosphates (CPP) powders may be made using methods that some of the inventors have disclosed previously, see Filiaggi M. J. et al., Bioceramics 11:341-344, 1998; and Pilliar R. M. et al., Biomaterials 22:963-972, 2001. Briefly this involves the calcining at 500° C. of calcium phosphate monobasic monohydrate [$Ca(H_2PO_4)_2.H_2O$] followed by melting the resulting powder at 1100° C. The powders are held in the molten state for one hour (to allow for limited CPP polymer chain growth) in a Pt crucible and the melt is then rapidly quenched to form a glassy frit that is ground and screened to give desired CPP powder sizes. For the gravity sintering studies, CPP powder of the selected size range was placed in small cylindrical Pt-10% Rh tubes and vibrated to give a packing density of approximately 55% full density. Sintering was undertaken in an air muffle furnace. Our prior experience had suggested that in addition to time and temperature, relative humidity at the time of sintering appeared to strongly affect sintering behaviour. The inventors, therefore, initiated a series of studies in which test samples were sintered under different humidity conditions (dependent on laboratory atmospheric conditions at the time; RH ~20%, 30%, 40% and 60% were used for our studies). The 4 mm diameter (nominal) rod samples resulting from sintering were cut into 2 mm lengths and the discs so formed were used to determine the properties of the sintered CPP. To determine the effect of sintering under different conditions, samples were analyzed to determine density (by weighing and measuring dimensions), crystal structure (XRD), and diametral compression or bend testing (to determine tensile strengths). In addition, samples were selected for examination by scanning electron microscopy (secondary electron imaging to determine structural features after sintering and back-scattered imaging of ground and polished sections to determine pore size distribution using a quantitative image analysis program).

Effect of Sintering Temperature on CPP Crystallization

Table 1 shows the results of the XRD studies from a series of experiments using powders of 75-106 μm size range sintered at different temperatures with relative humidity varying from 20 to 60%. (The selection of this particular size range for these studies was based on the results obtained in our ongoing tissue culture studies indicating that CPP substrates formed using this size range, if properly sintered, would form a suitable base for chondrocyte seeding and subsequent articular cartilage formation and anchorage [Waldman S et al, J Biomed Mater Res., 62:323-330, 2002]). Rod-shaped samples were formed as described above and, for this study, all samples were held at the selected sintering temperature for one hour. As noted, the results indicate that the relative humidity (RH) has an effect on the temperature at which the amorphous CPP powders crystallize. For a given holding time at temperature (e.g. 1 h), with increasing RH, crystallization (as determined by the appearance of peaks on the XRD spectra) occurs at lower temperatures (e.g. 590° C. @ 20% RH, 585° C. @ 30& 40% RH, and 580° C. @ 60% RH). We surmised that this was due to the effect of RH on the CPP polymer chain structure. Increased relative humidity would result in hydrolysis at oxygen-bridging sites resulting in shorter average chain length (i.e. lower average MW). This would be expected to result in easier chain mobility and, consequently, more rapid diffusion rates and transformation to a crystalline CPP form at lower temperatures.

TABLE 1

XRD results of the CPP specimens gravity-sintered at various temperatures for 1 h under different humidity condition
(a: amorphous; mc: minor crystallization; c: crystallized)

| SAMPLE | RH: 20% | RH: 30% | RH: 40% | RH: 60% |
|---|---|---|---|---|
| As made | a | a | a | a |
| 570° C. | a | a | a | a, mc |
| 580° C. | a | a, mc | a, mc | c |
| 585° C. | a | c | c | c |
| 590° C. | c | c | c | c |
| 600° C. | c | c | c | c |
| 625° C. | c | c | c | c |
| 650° C. | c | c | c | c |

FIG. 1 indicates another interesting difference for CPP samples sintered at temperatures below 700° C. compared to those sintered at 700 or 950° C. (all at RH ~30-40%). Additional diffraction peaks can be seen at the lower temperatures that disappear at higher sintering temperatures; (for example, a peak at θ-20° is observed to disappear on sintering at 700° C.). This suggests that phases other than β-CPP form during crystallization at these lower temperatures. It is also possible that some undetected amorphous zones (possibly at sinter neck regions) may have been retained at the lower temperatures (i.e. below 650° C.). The effect of these small differences were reflected in the mechanical and degradation properties as described below.

Effect of Relative Humidity on Sintering Rate

Figure 2:
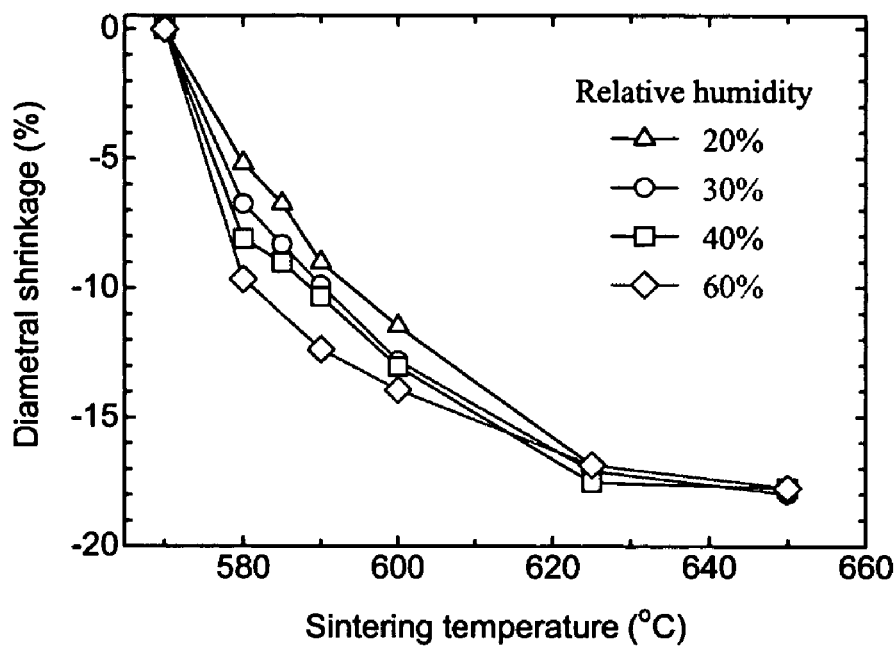
FIG. 2 shows diametral shrinkage of gravity-sintered CPP structures versus sintering temperature under different humidity conditions.

The inventors have studied and determined the effect of relative humidity on densification rate during sintering. For this study, 4 mm diameter rod-shaped CPP samples that were formed by sintering at 575 to 650° C. were used. Samples were raised to the selected sintering temperature using a specific heat-up schedule (10° C./min from RT to 500° C. and then at 5° C./min to the selected sinter temperature) and then held at each sintering temperature for a one-hour period. Three levels of RH (20%, 30%, and 40%) were investigated based on our previous observation that significant differences in crystallization kinetics resulted over these RH conditions. Diametral shrinkage of the rod-shaped samples was used as a measure of densification rate. The results are presented in FIG. 2. Increasing RH resulted in an increase in diametral shrinkage at all temperatures in the range studied (570 to 650° C.) with the difference in shrinkage rate (% shrinkage/° C.) becoming insignificant at temperatures above about 620° C. (and below 580° C.).

Figure 3:
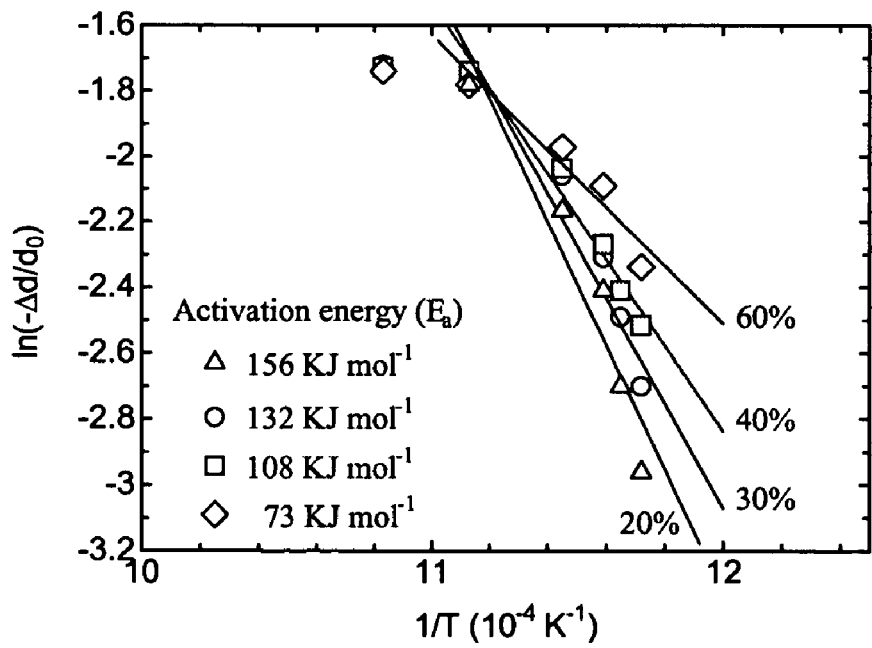
FIG. 3 shows an Arrhénius plot of the diametrical shrinkage ($\ln[-\Delta d/d_o]$) of gravity-sintered CPP specimens vs. temperature ($1/T$) under different humidity condition.

The effect of RH on activation energy was determined for sintering using a similar experimental arrangement but including higher (60%) RH conditions. This study allowed the inventors to investigate the differences due to RH variation and from the data the inventors calculated activation energies associated with CPP sintering in this temperature range as a function of RH. The results are shown in FIG. 3. The effect of RH on activation energy in the 580 to 620° C. range is apparent. While the inventors were unable to relate these activation energies to identified transport mechanisms for CPP molecules, the values suggest mechanisms consistent with low activation energy processes (surface diffusion or viscous flow (German R M, Powder Metallurgy Science, $2^{nd}$ edition, MPIF, 1994)). Due to the fact that shrinkage appeared to be negligible at temperatures above about 620° C. for all humidity levels studied (with the one hour sintering times used), the inventors did not include the 650° C. results in the calculation of activation energies. It was believed that a different sintering mechanism dominated above 620° C., one associated with sintering of well-crystallized CPP and having a higher activation energy (i.e. volume or grain boundary diffusion). Of significant note was the effect observed between 580 to 600° C., the temperature range over which the amorphous CPP transformed to a crystalline structure using the one-hour sintering time.

Figure 4:
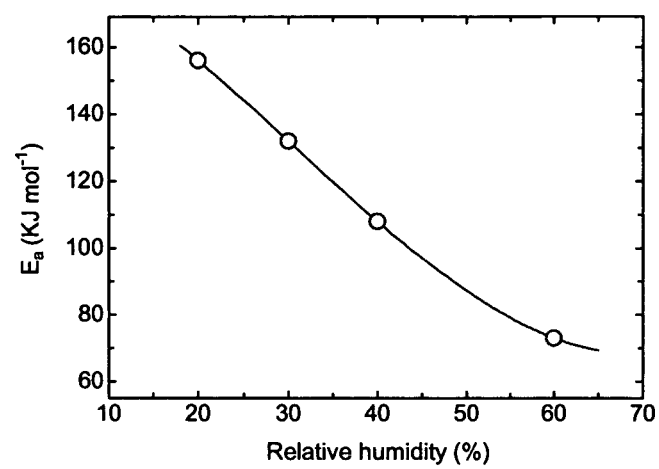
FIG. 4 is a plot showing variation of activation energy during gravity sintering of CPP ceramics vs. humidity.

FIG. 4 summarizes the effect of RH on activation energies for sintering in the 580 to 600° C. range. The results indicate that the activation energy is inversely proportional to relative humidity in the 20 to 60% RH range. This is consistent with the proposal that CPP chain scission due to hydrolysis results in easier chain mobility facilitating transport mechanisms responsible for sinter neck formation and growth.

Mechanical Testing of As-Sintered Samples

In some studies, disc-shaped samples were used for diametral compression testing to determine the tensile strengths of as-sintered samples. The final density of all sintered samples was ~65% full density. The results of the studies are presented in Table 2. Included in Table 2 are XRD results for the tested samples. Sintering at 585° C. and higher temperatures resulted in significantly higher strengths compared with the 580° C. sintered samples. This also corresponded to crystallization of the amorphous CPP. Also of note is the slight decrease in tensile strength for sintering temperatures above 600 to 650° C. As noted below, this corresponds to formation of coarser CPP crystals (within the CPP particles), with the lower sintering temperatures resulting in sub-micron-sized crystals and very fine sub-micron-sized pores at grain boundaries (due presumably to volume shrinkage upon crystallization). The finer structure resulting for sintering at temperatures between 585 and 650° C. would explain the slightly higher strength properties. As noted, at temperatures above 650° C. strength decreased. The difference between 700 and 950° C. sintered samples, however, did not appear to be significant. This is consistent with the proposed slow diffusion rates within crystalline CPP resulting in minimal sinter neck growth and densification as well as grain coarsening that was insufficient to result in a dramatic change in strength.

TABLE 2

Mechanical testing of as-made 75-106 μm CPP samples sintered at various temperatures

| Sintering temperature | DCS testing Tensile Strength (MPa) | |
|---|---|---|
| 580° C. | 7.28 ± 0.88 | Amorphous |
| 585° C. | 13.84 ± 1.43 | Crystallized |
| 590° C. | 13.64 ± 2.41 | Crystallized |
| 600° C. | 14.77 ± 3.63 | Crystallized |
| 650° C. | 12.39 ± 2.31 | Crystallized |
| 700° C. | 11.24 ± 1.75 | Crystallized |
| 950° C.* | 10.36 ± 2.72 | Crystallized |
| 950° C.* | 10.75 ± 1.96 | Crystallized |

*comparable results from two different batches of CPP

Scanning Electron Microscopic Examination of As-Sintered Samples

Figure 5:
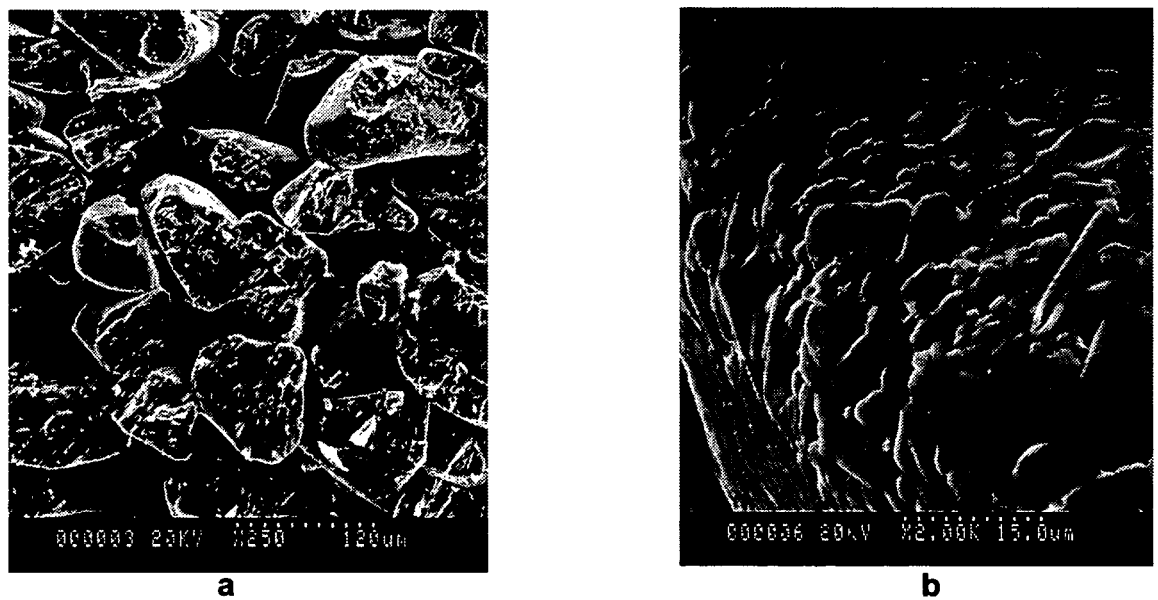
FIG. 5 shows scanning electron micrographs (SEM) of CPP samples as-sintered at 950° C.: a) fracture surface—low magnification, b) sintered surface at higher magnification showing grain structure within a CPP particle.
Figure 6:
FIG. 6 shows scanning electron micrographs of 650° C.-sintered CPP samples after diametral compression testing: a) fracture surface, b) higher magnification view of the sintered surface.
Figure 6:

Secondary electron SEM images of sintered CPP samples (950° C. sintering temperature) are shown in FIG. 5 (fracture surfaces and sintered surfaces). For comparison, surfaces of samples sintered at lower temperatures (600, 650 and 700° C.) are shown in FIG. 6. All these samples were formed using 75 to 106 µm size range CPP powders. The irregular but more or less equiaxed nature of the CPP particles is apparent (FIGS. 5*a*, 6*a*) as is the varied geometry of the sinter necks. Also evident are small sub-micron-sized pores at intergrain boundaries (FIG. 5*b*). The structure is characterized by interparticle pores in the 50 to 100 µm size range (suitable for bone ingrowth) and the much finer sub-micron-sized pores at intergrain boundaries. The individual crystals within the CPP particles were readily discernible for the 950° C. sintered samples (FIG. 5*b*). They ranged from approximately 1 to 5 µm in size. Crystals were not readily discernable in the low-temperature sintered samples. Based on prior TEM observations (Porter N et al, J Biomed Mater Res., 56:504-515, 2001), these are believed to be sub-micron-sized (~30-50 nm).

Mechanism of CPP Sintering and Design of Sintering Process for Reproducible Porous CPP Part Production The results of the sintering studies disclose herein indicate that rapid sinter neck formation and growth with the CPP powders occurred at temperatures between 585 and 600° C. with viscous flow or surface diffusion being the dominant mechanism (more likely viscous flow of the amorphous powders at temperatures just prior to nucleation of crystals). The temperature at which crystallization rate was significant was dependent on RH with high RH conditions resulting in crystallization at lower temperatures (580° C. or so using a one-hour hold) and low levels delaying crystallization (approximately 590° C. for the one-hour hold). Following crystallization, sintering rates were observed to be very low since other mechanisms with much higher activation energy for mass transport dominated. During preparation of porous CPP samples by sintering at 950° C. for one hour (the process selected for preparing samples for our early tissue engineering studies), we experienced variable success in achieving structures that were approximately 65 percent dense with interconnected pores of desired size, and in addition, were sufficiently strong (tensile strength>10 MPa in the as-sintered state). Two undesirable effects were under-sintering of CPP yielding low strength samples, and over-sintering giving samples with lower percent porosity and, in some cases, without the interconnected porous network. The results of our study have provided an explanation for these occurrences and, further, have allowed us to define processing parameters for reliably making samples of desired characteristics.

The under-sintered samples were formed under low RH laboratory conditions, (frequently occurring during the winter months). While this would be expected to result in higher crystallization temperatures, it would also result in slower rates of material transport including slower viscous flow and slower surface diffusion. Thus, less sinter neck growth would result during the finite time that samples were at temperatures just below the crystallization temperature during heating to the final 950° C. sinter temperature. This resulted in weaker, unacceptable sintered samples.

High RH laboratory conditions, gave the opposite effect. While these conditions resulted in lower crystallization temperatures (~580° C.), they also resulted in greater CPP chain mobility, greater viscous flow (and surface diffusion), and faster sinter neck growth of the amorphous CPP at temperatures just below the crystallization temperature. This resulted, in some cases, in grossly over-sintered structures with density greater than 80%.

Based on these results, the following processing schedule has been defined for forming CPP samples of suitable strength and density using 75 to 105µm-sized powders: Relative Humidity=30 to 40%, Heat @ 10° C./min to 500° C.+heat @ 5° C./min to 585° C. (Stage 1 sinter temperature), hold @ 585° C. for 1 hr+heat @ 10° C./min to between 700 and 950° C.+hold @ this temperature (Final sinter temperature) for 1 hr; cool to RT.

This heating schedule allows the sample sufficient time in the critical sub-crystallization temperature range to develop significant sinter necks and sample strength while maintaining the desired open-pored (65 volume percent density) structure.

For higher or lower RH conditions, the Stage 1 sinter temperature should be higher or lower respectively with possible adjustment in hold time. The preferred RH is 30 to 40%.

For sintering finer or coarser CPP powders, the Stage 1 and Final sinter temperature should be adjusted (particularly for finer powders for which these sinter temperatures should be lower).

The final sinter hold temperature, while not having a strong effect on density, does affect grain size and properties of the sintered CPP samples. The 950° C., one hour hold results in the formation of a microcrystalline CPP (crystal size ranging from approximately 1 to 5 µm). Using lower final sintering temperatures (just above the crystallization temperature for example), results in sub-micron-sized crystalline structures. Crystal size affects both initial strength and degradation rate of the porous CPP. We have explored this possibility using in vitro degradation studies as described below.

Formation of Dual Pore-Size Range Samples

Figure 7:
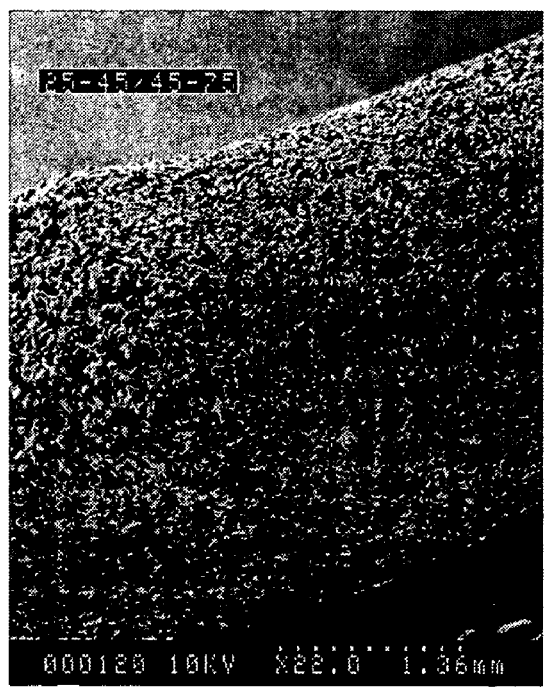
FIG. 7 shows scanning electron micrographs of sintered junction zone of a) 25-44/45-75 µm and b) 25-44/75-105 µm dual pore-sized samples.
Figure 7:
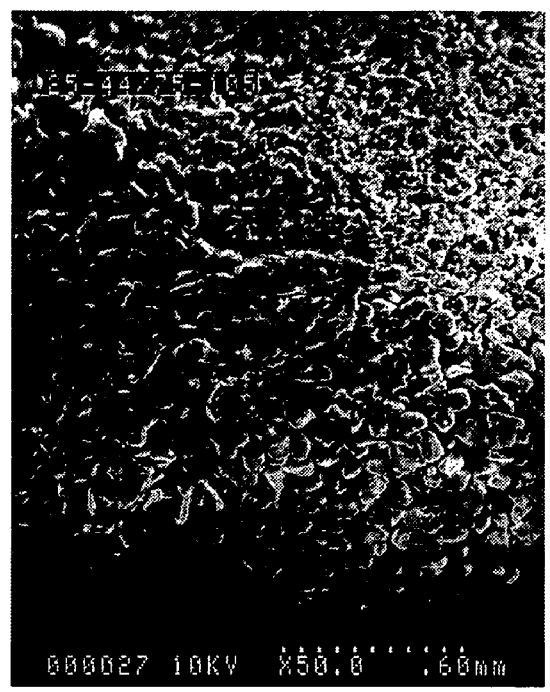

FIGS. 7*a* and 7*b* show scanning electron micrographs (SEM) of two different dual pore-size range samples (<44 µm/75-106 µm and 44-75 µm/75-106 µm). These samples were formed by first pre-sintering the larger pore size portion at below the crystallization temperature followed by the placement of the finer powders onto this first portion and then subjecting the whole sample to a second final sintering treatment (as determined by the sintering characteristics of the finer powders). Some mechanical tests to determine the fracture behaviour of samples so formed were undertaken. SEM examination of the boundary region between the two pore size fractions showed that there was some intermixing of the powders in this region. Fracture during testing occurred through this region as well as the fracture path diverging in regions into one size fraction portion or the other. The results suggest that dual pore-size components could be made if required using such a simple procedure.

Formation of Shaped Substrates

For the studies of sintering characteristics and in vitro cartilage tissue formation on CPP substrates we used simple disc-shaped samples. In order to use this method for the repair of osteochondral defects or for formation of other tissue-engineered CPP-based skeletal implants, it was necessary to develop methods for forming complex shapes of porous CPP. Two issues were addressed. First, in order to study the use of cartilage-CPP constructs for repair of osteochondral defects in vivo, we initiated an animal study in which defects were created in sheep knee joints and cartilage-CPP implants were implanted in these sites in order to investigate their use for defect repair. Initial attempts using cylindrical plugs proved problematic in terms of implant positioning and initial stabilization. Therefore, we repeated the studies using CPP shapes that were tapered. Truncated conical 'plugs' were considered best since these would be self-seating when pressed into an appropriately-prepared site thereby allowing the implants to be more easily placed to the proper depth. To form the tapered implants (taper angle ~5°), sintered cylindrical forms were machined to the desired shape. Both pre-forms (sintered at a temperature ~585° C., shaped, and then given a final sinter treatment), as well as finally sintered samples were shaped in this manner. Both methods proved equally acceptable for forming the tapered substrates. For the sheep osteochondral 'plugs', a 2 mm long superior straight-sided cylindrical portion was left above a 4 mm inferior tapered portion of the implant in our initial trials and in our second trial set, this straight portion was limited to the top 0.5 mm length (approximately) with the remainder of the implant being tapered at approximately 5°. The total length of this second set of tapered implants was ~7 mm.

The 4 mm diameter cylindrical form of the porous CPP samples was determined by the i.d. of the Pt-10% Rh tubular crucibles used for sintering. The choice of Pt—Rh crucible material for sintering CPP was based on its inertness and resistance to deformation (i.e. superior to Pt in resisting scoring and scratching, important for allowing easy removal of the sintered CPP cylinders). However, the disadvantage of this crucible material was its high cost. In order to make larger implants, the use of Pt—Rh crucibles was impractical in the present study. Therefore, the inventors investigated an alternative 2-stage approach for forming porous CPP parts of larger dimension or more complex shape. The first stage of processing used a low temperature pre-sinter treatment with the CPP powders being held in $Al_2O_3$ crucibles of desired dimensions. At the low pre-form sintering temperatures (~585° C. maximum), it was hypothesized that CPP powder—$Al_2O_3$ reactions would be negligible. This pre-sinter treatment resulted in porous CPP forms that could be handled, machined to a final desired shape and subsequently placed on Pt foils for the final ($2^{nd}$ stage) sinter. The method proved practical allowing large porous CPP shapes to be formed. Using this method, samples suitable for 3-point bend testing as well as the formation of complex forms for biphasic (i.e. tissue+CPP) implant formation were made.

Surface analysis using XPS of porous CPP cylinders formed using $Al_2O_3$ crucibles for stage-1 sintering have indicated no significant levels of Al (in the CPP) due to this processing. Cell culture studies have confirmed that the use of the $Al_2O_3$ crucibles for stage-1 sintering does not introduce any trace impurities that may compromise biocompatibility of the porous CPP forms preventing cartilage formation in vitro. Other crucible materials displaying good thermodynamic stability and relative inertness at temperature can also be used.

Degradation Studies of Sintered CPP

Both in vitro and in vivo degradation studies of porous CPP samples were undertaken. The in vivo tests involved implantation of 4 mm diameter×6 mm long cylindrical implants in rabbit tibia. The results of these studies have been published (Biomaterials, 23:2063-2070, 2002). Further in vivo studies of degradation of porous CPP osteochondral defect repair 'plugs' are in progress with studies of CPP implants formed using different Final sintering temperatures being investigated. This includes investigation of sub-micron-sized crystal samples (700° C. Final sinter) as well as micron-sized crystal samples (950° C. Final sinter).

The in vitro studies involved aging of porous CPP samples (made from 75 to 106 μm-range powders) i) in solutions simulating physiological environments but without chondrocytes, and ii) in the culture medium used for in vitro formation of cartilage both with and without the addition of bovine chondrocytes were undertaken to assess both the potential for CPP degradation in these solutions and its rate. Too rapid degradation in vitro is undesirable since this would result in unacceptably low mechanical strengths for components to be implanted. The in vitro studies using simulated physiological solutions involved placement of 4mm diameter disc-shaped samples in 0.1 M tris-buffered solution at a pH of 7.4 and aging at 37° C. for 1, 5, 10, and 30 day periods with continual agitation of the solution. Aging in cell culture medium (with and without cells) was done for a period of 8 weeks. Following in vitro aging, the density of the samples was measured and diametral compression testing performed. Selected samples were examined by scanning electron microscopy following testing. The results of in vitro aging for porous CPP samples (75 to 105 μm powder size) prepared using different sintering temperatures are presented in Table 3. From Table 3, it is apparent that, in general, samples sintered at lower temperatures (below 650° C.) display greater degradation. This is presumably a result of the finer grain size presented by these materials or possibly to their less developed β-CPP crystallinity. Interestingly, the 700° C. sintered samples were observed to be more stable and to degrade to a lesser extent based on these initial tests. The optimal final sintering temperature is determined by the best combination of initial strength and desired degradation rate.

Figure 8:
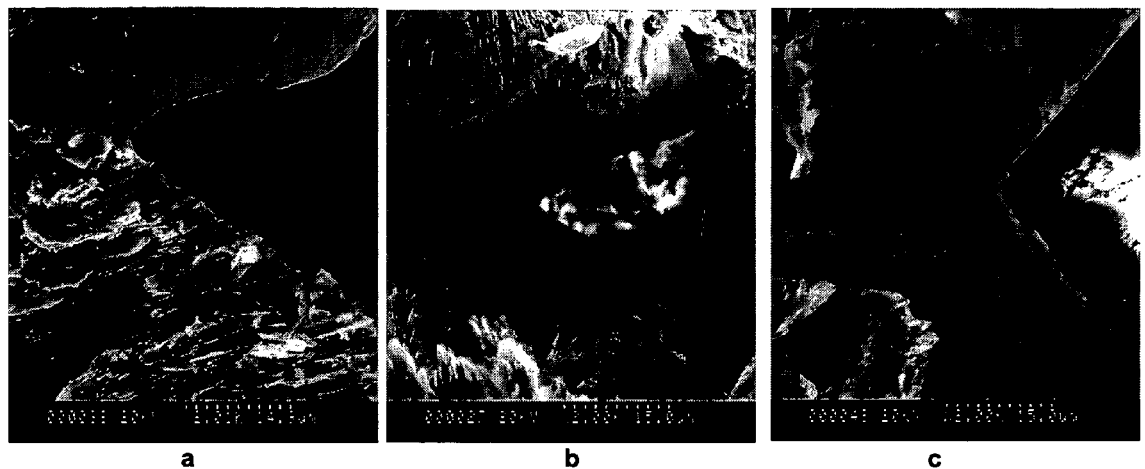
FIG. 8 shows scanning electron micrographs (2000×original magnification) of low-temperature-sintered samples aged for 30 days in tris-buffered solution at 37° C.: a) sintered at 600° C./1 h, b) sintered at 650° C./1 h, c) sintered at 700° C./1 h.
Figure 9:
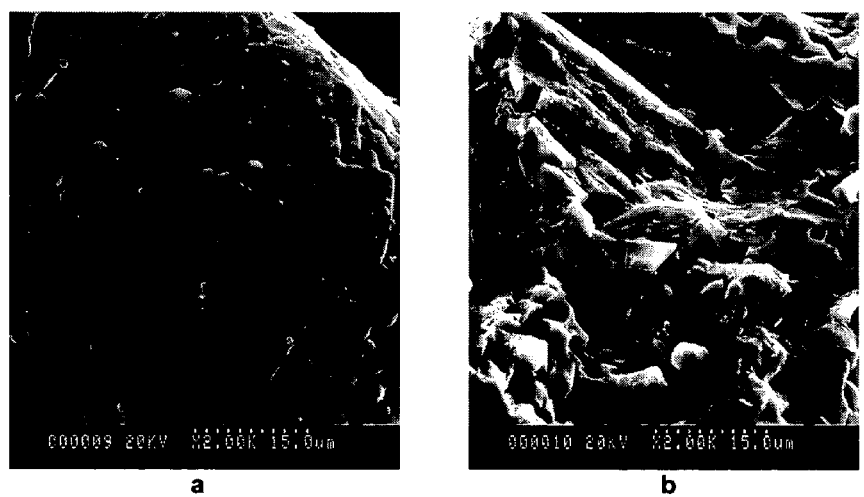
FIG. 9 shows scanning electron micrographs of 950° C.-sintered sample after aging in tris-buffered solution for 30 days at 37° C.: a) sintered surface, b) fracture surface (Original magnification=2000×)

Representative SEM images of low-temperature-sintered sample structures after aging for 30 days are shown in FIGS. 8 (a-c). These reflect the more rapid and extensive degradation of the low-temperature-sintered samples compared with those sintered at 950° C. (FIG. 9). Studies are in progress to develop a better understanding of the mechanism of degradation. Presumably, degradation effects are concentrated at grain boundary zones which would support the observation of slower degradation rates for the 700 and 950° C. sintered samples.

TABLE 3

Diametral compressive strength (MPa) of 75-105 μm CPP structures sintered at different temperatures after periods of in vitro degradation:

|  | 0 day | 1 day | 5 days | 10 days | 30 days |
|---|---|---|---|---|---|
| 950° C. | 10.75 ± 1.96 | 7.16 ± 1.48 | 6.43 ± 1.20 | 5.61 ± 1.29 | 5.43 ± 1.15 |
| 590° C. | 13.64 ± 2.41 | 6.70 ± 2.78 | 3.82 ± 0.74 | 4.40 ± 1.91 | 5.62 ± 1.77 |
| 580° C. | 7.28 ± 0.88 | 2.93 ± 0.51 | 1.94 ± 0.47 | 1.56 ± 0.19 | 1.64 ± 0.42 |
| 600° C. | 14.77 ± 3.63 | 6.90 ± 0.90 | 3.30 ± 0.67 | n/a | 3.82 ± 0.62 |
| 650° C. | 12.39 ± 2.31 | 7.81 ± 1.43 | 6.48 ± 1.29 | n/a | 5.32 ± 0.95 |
| 700° C. | 11.24 ± 1.75 | 10.23 ± 2.12 | 9.39 ± 1.36 | n/a | 6.90 ± 1.38 |

A second approach for controlling degradation rate of porous CPP involves modifying their composition through doping with other cations such as $Na^+$, $K^+$, $Ti^{4+}$, $Mg^{2+}$. This also has an effect on the processing conditions used for forming the sintered porous structures through an effect on the rate of crystallization of the amorphous inorganic phase (see additional information presented below).

Figure 10:
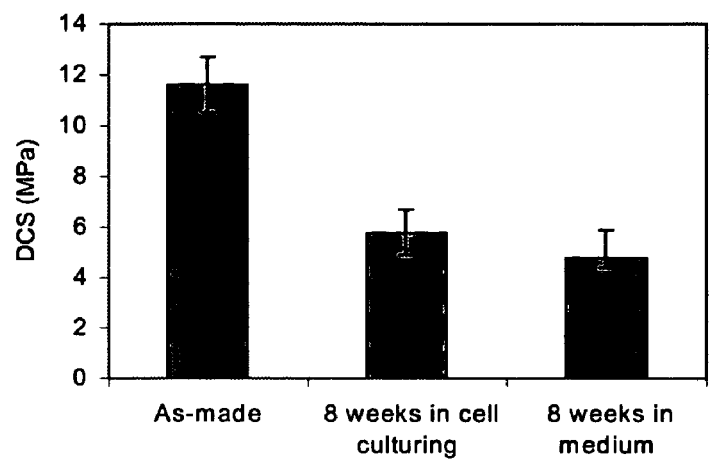
FIG. 10 shows diametral compression strength, the effect of aging in cell culture medium.

As noted above, in addition to the aging studies in tris-buffered solution, we also investigated porous CPP degradation (950° C.-sintered form) in culture medium with and without chondrocytes. The results of these studies are summarized in Table 4 and FIG. 10. The CPP samples used in these studies were made with 45-75 μm powders. We concluded that after placement in the medium for an 8-week period (the period used for forming cartilage in vitro), the high-temperature sintered samples retained sufficient strength to allow their use as implants following in vitro cell culture processing. The percent degradation in the presence of cells was equal to 50%, and in the absence of cells, 58% leaving samples with tensile strengths ~5 MPa. The slightly higher strengths in cell-containing culture medium was thought to be due to new tissue formation affecting the diametral compression testing.

TABLE 4

DCS degradation result of 45-75 μm CPP disks after tissue culturing and aging in medium (20% F12):

| As-made DCS | After 8 weeks in Cell-culturing | After 8 weeks in medium |
|---|---|---|
| 11.6 ± 1.1 MPa | 5.8 ± 0.9 MPa | 4.82 (+1.5/−0.5) Mpa |

Effect of Doping on Processing of Porous CPP-Based Structures

Addition of trace amounts (for example, 0.1 to 1.0 mol %) of cation additives using $TiO_2$, $Na_2O$, $K_2O$, MgO mixed into the starting calcium phosphate monobasic monohydrate powders during preparation of CPP, results in a 'doped' CPP material displaying a slower rate of crystallization. This has an effect on both the rate of cooling necessary to form an amorphous starting powder (slower rates of cooling are possible compared with the rapid quenching required with pure CPP), and the crystallization (devitrification) temperature (higher than for pure CPP) allowing a greater range of temperature for sinter neck formation and growth through viscous flow prior to crystallization. By example, crystallization of $TiO_2$-doped CPP (0.1 mole %) occurs at 683° C. vs 642° C. for pure CPP as determined using Differential Thermal Analysis (DTA). Melting temperature as determined by this method also is lower for the 0.1 mole % $TiO_2$-doped CPP (957° C. vs 986° C.).

In Vitro and In Vivo Experiments with Pure CPP—Tissue Formation and Biological Response A brief summary of our findings on the effect of pore size as well as the use of $Al_2O_3$ crucibles for pre-form fabrication during the 2-stage sintering process follows is as follows. Prior studies using porous $Ti_6Al_4V$ samples indicated that finer pore-sized discs resulted in thicker cartilage layers being formed and anchored to the porous discs. Therefore, we investigated the effect of varying the pore size of CPP porous discs. Four CPP powder size ranges (45-75, 75-106, 106-150, and 150-250 μm size ranges) were used to form discs that were defined as fine-, medium-, coarse- and very coarse-pore sized. (Only a few samples of the 150-250 size range were tested since they appeared to vary too much in overall dimensions and tended to be most susceptible to particles breaking off during handling). For the other three size ranges, our cell culture studies (8-week in vitro cultures) indicated that there were no significant differences in the cartilage tissue that formed. In view of the fact that bone ingrowth (as required in the subchondral region of osteochondral 'plugs') was favoured by pores in the 50 to 100 μm size range, we chose for our studies to focus on samples made from 75 to 106 μm-sized powders.

The cartilage layers that formed in 4- to 8-week periods in vitro varied in overall thickness from approximately 1 to 2 mm. Biochemical analysis demonstrated the molecular constituents of native articular cartilage (Type II collagen predominantly and proteoglycans-PG) but with a lower collagen:PG ratio (~1:1 vs 3:1). It was believed that this was due to the very immature form of the newly-formed cartilage (i.e. only 4- to 8-weeks old). Studies on modifying culture conditions (composition or mechanical stimulation during cartilage formation) are ongoing. Results to date have indicated some improvement in cartilage characteristics can be achieved with appropriate in vitro manipulation.

Based on what were considered successful preliminary in vitro results, as well as the ability to reliably make porous CPP forms of desired shape and properties (65 volume % porosity, pore size range ~50 to 100 μm, tensile strength after in vitro processing >5 MPa), we proceeded to make samples for implantation in cartilage defect zones created in sheep knee joints. In our first series of animals using implants with tapered bone interfacing forms, the biphasic (cartilage-CPP) constructs were press-fitted into prepared sites and left for 3 months prior to animal sacrifice.

Formation of Crystalline+Amorphous CPP Composites

In order to form porous CPP structures with some definite amorphous regions incorporated within and coupled to the crystalline porous CPP structures, the following process was developed.

First, a porous crystalline CPP part is formed by sintering coarser powders (e.g. 150 to 250 μm) using either the process described herein. (e.g. heat @ 10° C./min to 500° C.+heat @ 5° C./min to 585° C. (Stage 1 sinter temperature), hold @ 585° C. for 1 hr+heat @ 10° C./min to between 700 and 950° C.+hold @ this temperature (Final sinter temperature) for 1 hr; cool to RT) or a variant of it that also results in a porous CPP structure. This procedure results in a structure that may, for example, be 65% dense (or greater density if appropriately processed).

Secondly, a much finer amorphous CPP powder (e.g. <44 μm) is mixed into either a water, or preferably, alcohol carrier (or acetone) and the sintered porous part is soaked in this to allow the fine CPP particles to be distributed more or less uniformly throughout the pores of the porous CPP and to be deposited onto the surface of the crystalline CPP following evaporation of the liquid carrier.

Figure 11:
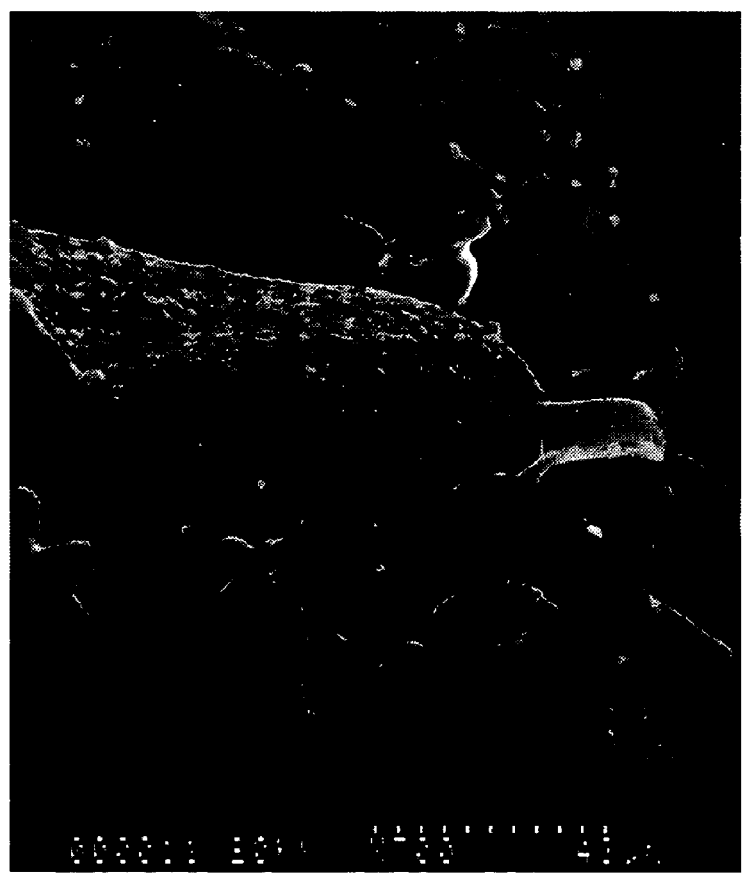
FIG. 11 shows a scanning electron micrograph of crystalline porous CPP formed by stage 2 sintering at 950° C. for 1 h of 150 to 250 micron-sized powders followed by infiltration of fine (25 to 44 micron) amorphous CPP powders into the pores and sintering at 570° C. for 1 h. The small amorphous powders are observed to bond securely to the coarser crystalline CPP thereby forming a porous composite of crystalline and amorphous CPP.

Thirdly, the amorphous CPP+crystalline CPP is given an additional sinter treatment but with the sinter temperature and time being chosen to be above the glass softening or glass transition temperature but sufficiently low and for short enough time to prevent the crystallization of the fine CPP particles. The resulting structure is a composite of crystalline and amorphous CPP as shown in FIG. 11. This results in a porous structure with regions that will degrade much more rapidly in vivo thereby releasing $Ca^{2+}$ and $PO_4^{3-}$ at faster rates from these regions while still retaining the initial integral porous CPP structure more or less.

Summarizing, the determination by the inventors of the mechanism acting during sinter neck formation of sintered CPP powders and the effects of relative humidity on this has resulted in the design of sintering schedules for reliable formation of porous CPP parts. As a result both monolithic porous CPP components to be used for forming tissue-engineered implants (particularly ones involving soft tissue-to-bone attachment), and interpenetrating phase composites made of biodegradable inorganic-organic constituents are possible.

The powders to be used for forming the desired porous structures should be amorphous at low temperature and with an appropriate size distribution and particle shapes to allow the powder particles to be packed into a 'green' compact either by gravity (with appropriate vibration of powders) or with the use of pressure. Upon heating, the powder should remain in a glassy (amorphous) state to a temperature sufficiently high that significant viscous flow of the material will occur to allow the formation of significant sinter neck junctions between particles. This occurs above a so-called glass transition temperature, $T_g$, or glass softening temperature, $T_s$ (these may be different but they both define a similar event, namely the temperature at which significant viscous flow of the glassy material occurs). At a temperature somewhat higher than this temperature, crystallization (or devitrification) of the glassy structure occurs. If this temperature is reached during sample heating so that densification due to sintering is limited while sinter neck formation is significant, the formation of a strong but open-pored structure is possible and this defines the desired outcome of the process described herein. Any material that satisfies this should be suitable for forming open-pored structures utilizing viscous flow as the major mechanism for achieving sinter neck formation and growth. The densification that occurs during this process will be limited to ensure that the open-pored structure with a 3-dimensional interconnecting network of pores is retained.

As noted above, different cationic dopants can be used to alter the final properties and the recommended processing schedule for forming porous CPP structures. That is, through the addition of trace amounts (up to about 1.0 mol % or the solubility limit for the dopant in CPP) of cation additives using $TiO_2$, $Na_2O$, $K_2O$, MgO mixed into the starting calcium phosphate monobasic monohydrate powders during preparation of CPP, a 'doped' CPP material displaying a slower rate of crystallization results. This has an effect on both the rate of cooling necessary to form an amorphous starting powder (slower rates of cooling are possible compared with the rapid quenching required with pure CPP), and the crystallization temperature (higher than for pure CPP) allowing a greater range of temperature for sinter neck formation and growth through viscous flow prior to crystallization. By example, crystallization of $TiO_2$-doped CPP (0.1 mole %) occurs at 683° C. vs 642° C. for pure CPP as determined using Differential Thermal Analysis (DTA). Melting temperature as determined by this method also is lower for the 0.1 mole % $TiO_2$-doped CPP (957° C. vs 986° C.).

Inorganic Porous Ceramic/Polymer Composites

The present invention also provides novel composite materials based on porous ceramic materials infiltrated with polymers that can form ionic bonds with the ceramic material once infiltrated into the porous ceramic. The inventors have unexpectedly discovered that the mechanical strength of porous ceramic materials can be significantly increased by infiltrating those polymers into the porous ceramic material that are capable of forming ionic bonds with the ceramic material.

The inventors have formed composite structures consisting of interpenetrating CPP and biodegradable (i.e. bioresorbable) organic polymer constituents, although there is no specific limitation on the use of biodegradable organic polymers alone but rather the type of polymer used will depend on the application for the composite. Preferably, the polymers are designed to a) interact with the CPP substrate and 'wet' the CPP during the infiltration process, and b) to promote strong chemical bonding with the CPP.

Development of Biodegradable (i.e. bioresorbable) Interpenetrating Phase Composites While the organic phase of the IPC can be selected from among many polymers including but not limited to the following list: polycarboxylates, polysulfates, polysulfonates, polyphosphates, polyamines, polyurea, polyamides, polyalkylene oxide diols, polyalhylene oxide diamines, polycarbonate, polylactone, polyethersulfone, polyvinyls, polypeptide; polysaccharide; polyurethanes, polysulfones, polycarbonates, polyesters, polyethylene, polypropylene, polystyrene, polysilicone, poly(acrylonitrile-butadienestyrene), polybutadiene, polyisoprene, polymethylmethacrylate, polyvinylacetate, polyacrylonitrile, polyvinyl cloride, polyethylene terephtalate, cellulose and other polysaccharides, polysilicones, polyolefins, polyvinyl derivatives, polypeptide derivatives and polysaccharide derivatives, the preferred materials will consist of vinyl monomers and their derivatives, with or without the combination oligomeric vinyl monomers containing functionality such that the oligomeric portion has chemical features similar to any of the following: polycarboxylates, polysulfates, polyphosphates, polyamines, polyurea, polyamides, polyalkylene oxide, polycarbonate, polylactone, polyethersulfone, polyvinyls, polypeptide polysaccharide; polyurethanes, polysulfones, polycarbonates, polyesters, polyethylene, polypropylene, polystyrene, polysilicone, poly(acrylonitrile-butadienestyrene), polybutadiene, polyisoprene, polymethylmethacrylate, polyvinylacetate, polyacrylonitrile, polyvinyl cloride, polyethylene terephtahate, cellulose and other polysaccharides, polysilicones, polyolefins, polyvinyl derivatives, polypeptide derivatives and polysaccharide derivatives. The vinyl monomers and their oligomers can have multi-vinyl group function for introducing cross-links or they can be monomeric in terms of active vinyl group function. Examples of such molecules include but are not limited to triethylene glycol dimethacrylates, urethane dimethacrylates and bis-phenol A derivatives of dimethacrylates.

EXAMPLE

Interpenetrating Phase Ceramic/Polymer Composite

Figure 12:
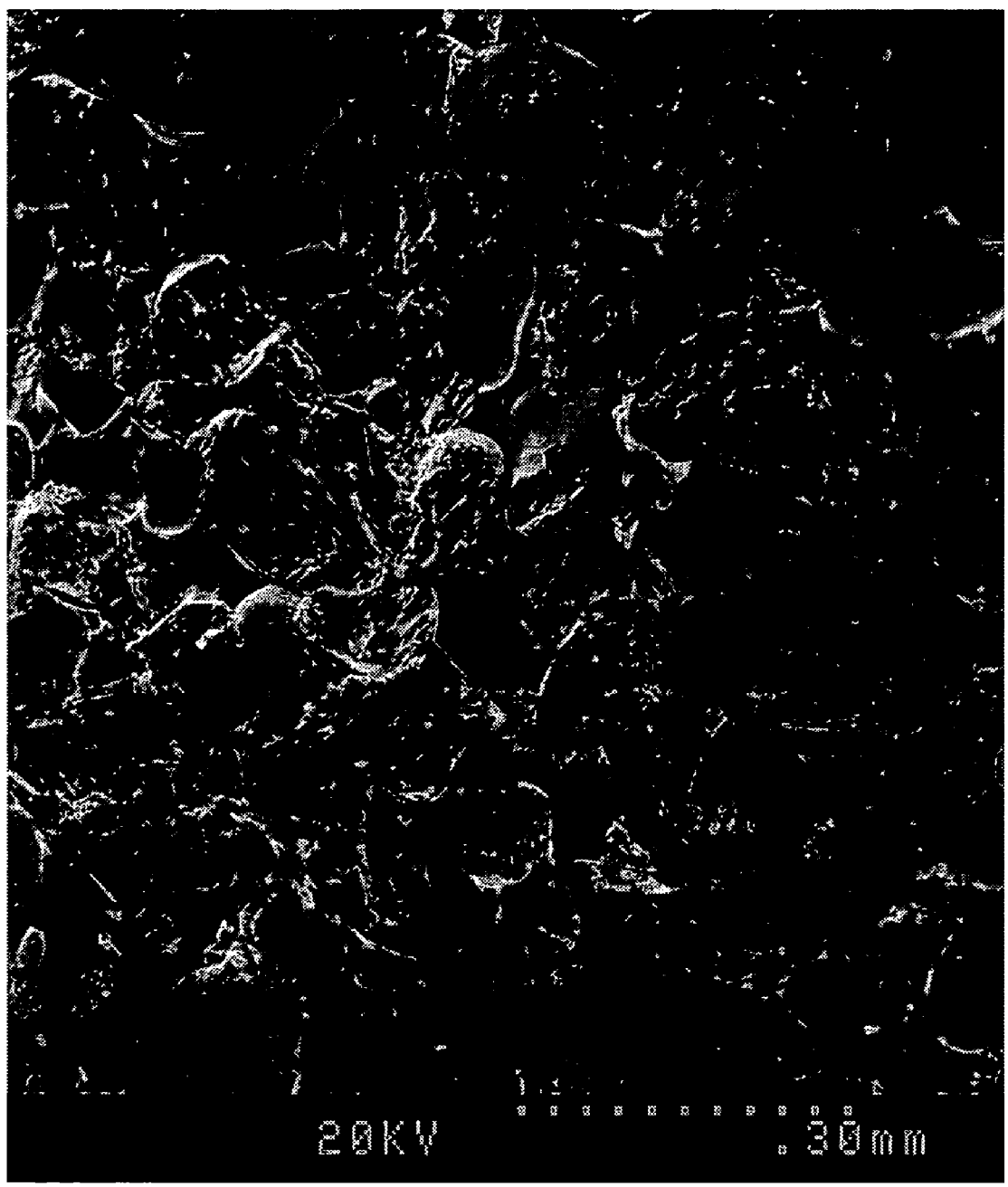
FIG. 12 shows a scanning electron micrograph of a fracture surface of a CPP-PVA-C (polyvinyl alcohol-carbonate) IPC showing the completely filled pores of the initial ceramic (CPP) with the infiltrated polymer (PVA-C)

An example of a fracture surface of such an Interpenetrating Phase Composite (IPC) is shown in FIG. 12. The scanning electron micrograph shows a 65% dense CPP sample that has been infiltrated with a biodegradable polymer resin synthesized from a polycarbonate (PCN) based divinyl oligomer and vinyl monomers containing ionic groups such as methacrylic acid (MAA). A number of resins formed with different ratios of PCN and MAA have been used for infiltration. Formulations exhibiting sufficiently low viscosity to flow into the porous CPP structures were selected and following infiltration into the porous CPP, were polymerized by heating to 80° C. or so.

One objective of the study disclosed herein was to develop a biodegradable polymer resin that could be utilized for the fabrication of an interpenetrating phase composite (IPC) made of porous calcium polyphosphate (CPP) and an organic polymer resin. The resin was synthesized from a polycarbonate (PCN) based divinyl oligomer and monomers containing ionic groups as described below. The ionic groups resulted in strong primary chemical bonding between the polymer and the CPP. Preliminary mechanical properties of the IPC were investigated by determining bending strength using a three-point bending test. The data showed a 7-fold increase in strength over that of the monolithic porous CPP and the addition of more ionic groups into the resin led to a higher bending strength for the newly formed CPP/polycarbonate resin system. Sample cross sections of the IPC examined using scanning electron microscopy (FIG. 11) suggested that the resin had infiltrated virtually all of the pores of the CPP.

Details of the method of forming the polyvinyl alcohol-carbonate resin (PVA-C) have been presented above. To form the porous CPP, CPP glass powders were prepared as described previously[2] by calcining calcium phosphate monohydrate, Ca $(H_2PO_4)_2 \cdot H_2O$ (J. T. Baker, Phillipsburg, N.J.) at 500° C. followed by melting the resulting powder in a Pt crucible at 1100° C. The molten CPP was rapidly quenched in distilled water to form a glassy frit. The frit was ground and screened to produce CPP particles of desired size. A size range of 106-150 μm was selected for use in this study. Porous CPP structures were produced by gravity sintering the amorphous CPP powders within Pt crucibles to form 20 mm diameter disc samples of approximately 35 volume percent porosity. Interconnected pores of up to 100 μm in size formed throughout.

The interpenetrating phase composites were prepared using the PVA-C resins and porous CPP structures formed as described above. Sintered CPP discs (with 35 volume percent porosity) were placed into Teflon wells (22 mm in diameter and 5 mm in height) and uncured resin was added into the disc-containing wells to completely immerse the disc allowing the resin to infiltrate the pores within the CPP discs. The infiltrated discs were cured as previously described, followed by one day cooling. Alternatively, the infiltration can be achieved by placing the porous CPP samples onto uncured low viscosity resin contained in a Teflon mould just slightly larger than the CPP sample and then gently pressing the porous CPP into the resin phase. The resin then infiltrates the porous CPP. The Teflon mould is placed in an oven and the resin is cured at 80° C. or so as previously described. Any excess resin is then removed by grinding from the outside surface. Other methods of resin incorporation are also possible. Due to the nature of the resin phase and the available reactive ionic groups, wetting of the CPP surface and ionic bonding presumably with the $Ca^{2+}$ and $PO_4^{3-}$ CCP ions occurs rapidly. The resulting composite material may be machined to a desired shape and form while retaining suitable mechanical strength and fracture resistance as a result of the good damage tolerance of the interpenetrating phase composite thereby minimizing micro-crack formation and growth during machining.

A detailed description of the method for forming the resin follows.

Synthesis and Characterization of the Oligomeric Divinyl Monomer.

The oligomeric divinyl monomer is made of 2 or more components consisting of a vinyl derivative such as methacrylic acid, hydroxyethylmethacrylate or other such vinyl monomer derivatives that can be coupled to oligomeric organic chains via classical condensation or substitution type reactions that would be known to those skilled in the art. The vinyl monomer may be reacted directly to isocyanate, amine, carboxylic acid, sulfonic acids, acid chloride or aldehyde groups located on the oligomeric molecules to yield oligo-amides; oligo-urethanes, oligo-ureas, oligo-sulfonates, oligo-sulfonamides; oligo-esters, oligo-acetal, oligo-imines.

The second group of components consist of the oligomeric elements and may include but are not limited to:

| Diisocyanates coupling agents | Oligomeric diol and diamine components | Alternate coupling agents |
|---|---|---|
| 2,4 toluene diisocyanate | Polycarbonate | Butane diol |
| 2,6 toluene diisocyanate | Polysiloxanes | Ethylene diamine |
| methylene bis (p-phenyl) diisocyanate | Polydimethylsiloxanes | Hexamethylene diamine |
| 1,5 naphthalene diisocyanate | Polyethylene-butylene | Hexamethylene dicarboxylic acid |
| 3,3' bis-toluene diisocyanate | Polyisobutylene | Lysinate |
| lysine diisocyanato esters | Polybutadienes | Hexane diol |
| 1,6 hexane diisocyanate | Polyesters | 2,5 diaminobenzene-sulfonic acid |
| 1,12 dodecane diisocyanate | Polyethersulfones | 4,4'diamino 2,2'-biphenyl disulfonic acid, 1,3-diamino 2-hydroxypropane |
| isophorone diisocyanate | Polyurethane | |
| cyclohexyl diisocyanate | Polyurea | |
| bis methylene di (cyclohexyl isocyanate) | Polyamide | |
| trimethyl-1,6 diisocyanatohexane | Polyalkylene oxide | N-(2-amino-ethyl)-3-aminopropane sulfonate |
| | Polyvinyl derivatives | |
| | Polypeptide derivatives | |
| | Polysaccharide derivatives | |
| | Polypropylene oxide | Dihydroxy vinyl derivatives |
| | Polyethylene oxide | Dihydroxy diphenylsulfone |
| | Polytetramethylene oxide | Hexamethylene diol |
| | Polyethylenebutylene | 1,5 pentanediol |
| | | 2,2-dimethyl-1,3 propanediol |
| | | 1,2-diamino-2 methylpropane |
| | | 3,3,-diamino-N-methyldipropylamine |
| | | 1,4 diaminobutane |
| | | 1,7 diaminoheptane |
| | | 1,8 diaminooctane |
| | | glutary dichloride |
| | | adipoyl dichloride |

A typical divinyl oligomer synthesis: Poly(1,6-hexyl 1,2-ethyl carbonate) diol (PCN, 750, Stahl Corp., Peabody, Mass.) was selected as the base component to synthesize the divinyl oligomer. The PCN based divinyl oligomer was synthesized using 1,6-hexane diisocyanate (HDI) (Aldrich, Milwaukee, Wis.) as a coupling agent to combine PCN with hydroxyethylmethacrylate (HEMA) (Aldrich, Milwaukee, Wis.). Before the synthesis, HDI and HEMA are distilled under vacuum whereas PCN is degassed overnight under vacuum at 30° C. The solvent used in the synthesis reaction is N,N-dimethylacetamide (DMAC) (Aldrich, Milwaukee, Wis.). To enhance the reaction rate, dibutyltin dilaurate (DBDA) is used as a catalyst in the reaction. The synthesis is carried out under dried $N_2$ gas. The PCN is dissolved in DMAC at 65° C. and then reacted with HDI in a 1:2molar ratio with 0.01 mL DBDA. The concentration of total reactants in the prepolymer step is 20% (w/v). The reagents are allowed to react for five hours at a temperature of 60-70° C. This is then followed by the addition of distilled HEMA along with 0.01 mL DBDA. The vinyl-coupling step is allowed to progress for four hours in a temperature range of 60-70° C. The final mixture is stirred overnight between 50-60° C. The reaction product is precipitated into an ether/distilled water mixture (30/70 v/v). The precipitated oligomer was recovered in the water layer and DBDA is extracted into the ether layer. The white product is subsequently washed five times with water before being dried in a vacuum oven at room temperature.

Synthesis and Characterization of the Cross-Linked Polymer Resins

The resin mixtures used for the preparation of the composite polymers were composed of the PCN-based divinyl oligomer along with different amounts of methacrylic acid (MAA) (Aldrich Chemical Co., Milwaukee, Wis.). Ionic containing oligomers may also include but are not limited to; methacrylic acid derivatives (including amino-acid derivatives), 2(methacryloyloxy)ethyl phosphate, 2-(methacryloyloxy)ethyl succinate, [3-(methacryloylamino)propyl]trimethyl ammonium chloride, 2-(methacryloyloxy)ethyl] trimethylammonium methyl chloride. The presence of divinyl function in the PCN oligomer produced a cross-linked three-dimensional network via free radical polymerization. The initiator used in this study, benzyl peroxide (BPO) (Aldrich Chemical Co., Milwaukee, Wis.) was used as received. Other chemical initiator systems may be used, including but not limited to: 1,1'-azobis(cyclohexanecarbonitrile); As well, light curing systems may be used to polymerize the vinyl resins, including but not limited to photopolymerizations initiated with camphorquinone (CQ, initiator) and 2-(dimethylamino) ethyl methacrylate (DMAEM, co-inititor).

Two examples of different formulations for the resin were studied and were produced using PCN divinyl oligomer: MAA molar ratios of 1:10 (polymer resin 1, PR1) and 1:20 (polymer resin 2, PR2). The mixture of monomer was stirred at room temperature until the PCN divinyl oligomer was completely dissolved in the MAA and then the initiator was added and mixed thoroughly yielding the polyvinyl alcohol-carbonate (PVA-C) resin phase. In all cases, the amount of BPO initiator was fixed at 0.2% (w/w) of the total mixture. The polymerization was carried out in an air-circulating oven and the reagents were contained in glass tubes under a $N_2$ atmosphere. The reagents were initially maintained at 60° C. for two hours and then the temperature was gradually increased to 80° C. where it was maintained overnight. The samples were then allowed to stand at room temperature for at least one day prior to any characterization. The resulting samples were yellowish and semi-transparent.

Formation of Interpenetrating Phase Composites (IPCs)

Figure 13A:
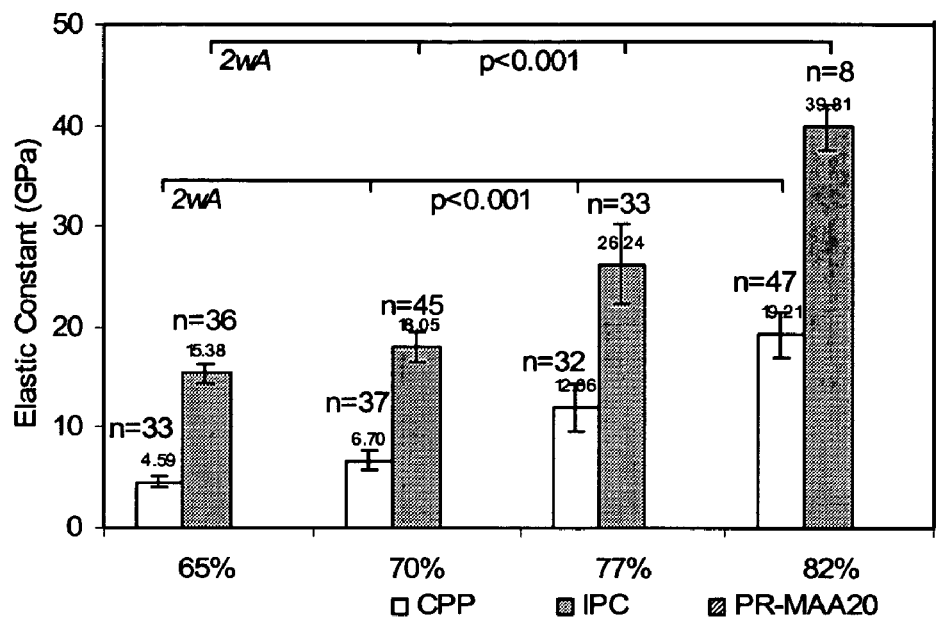
FIG. 13 shows bar graphs showing bending strengths and elastic constants of porous CPP of different starting densities and IPCs formed by infiltrating such porous CPP samples with an organic resin (PVA-C).
Figure 13B:
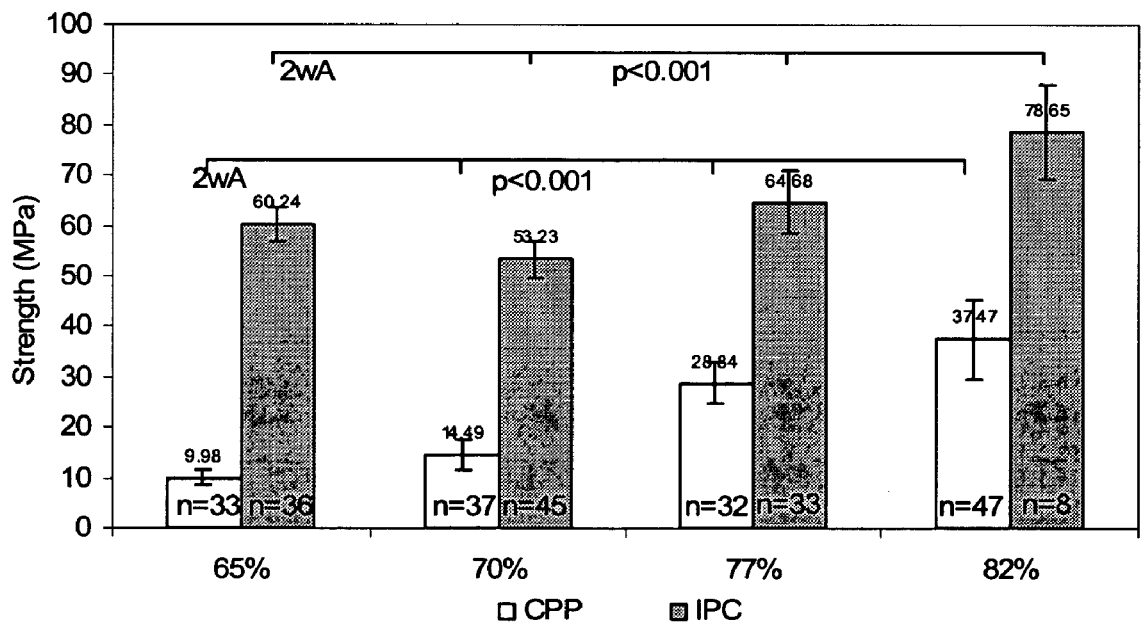

The CPP-PVA-C interpenetrating phase composite is formed by infiltration of the uncured resin phase throughout the interconnected pores of the sintered CPP. The uncured organic phase has to display sufficiently low viscosity to allow this infiltration. Infiltration is achieved by osmosis and capillary action or through pressurization. The polymeric resin phase is subsequently heat cured in situ (at 80° C. or so) within the CPP construct to yield the IPC. Subsequently, this material can be machined to a desired shape. This describes briefly the method for forming a biodegradable IPC for possible use in fields such as orthopaedics where implants used in bone fracture repair, for example, can be made from such material. An example of the resulting mechanical properties of such IPC materials is shown in FIG. 13. Also shown in this figure are examples of IPCs formed using sintered CPPs of different density. The different CPP density is readily achieved through selection of appropriate sintering schedules as taught through the present invention to allow the desired amount of densification.

The formation of the IPC structures involving infiltration of organic polymers throughout a pre-sintered porous inorganic structure is not limited to the CPP-PVA-C composites described above. Other biodegradable/resorbable or non-biodegradable/resorbable polymers with the required properties of low viscosity and ability to be polymerized in situ within the porous ceramic structures can be used with other inorganic phases (either biodegradable/resorbable or non-biodegradable/resorbable). Examples of other possible ceramic phases for use in forming porous substrates for infiltration to form IPCs are $Al_2O_3$, hydroxyapatite, MgO, $ZrO_2$, PSZ $ZrO_2$, $SiO_2$-containing ceramics and glasses, calcium sulphate-based materials, porous concrete, and any other ceramic although these may be formed using conventional, well known methods for sintering ceramic particles (i.e. not relying on viscous flow sintering mechanisms prior to crystallization).

While the above examples used ionic monomers which cured to give polymers which form ionic bonds to the inorganic phase, it will be understood that ionic monomers are not required in the case where the polymer is selected to covalently bond to the inorganic matrix. In this case the inorganic substrate may be first treated with vinyl coupling agents such as silanizing agents (including but not limited to agents such as methacryloxy propyltrimethoxysilane). The latter agents contain silane groups that will readily react with water to yield silanol groups that then undergo condensation reactions with free hydroxyl or other nucleophilic groups on the porous matrix in order to couple to the latter. The residual pendant vinyl group on the coupling agent can then undergo polymerization with the vinyl monomers of the infiltrated resin to yield covalent binding of the cured polymer to the porous matrix.

In the two cases of producing composites where either the polymer material is 1) selected to ionically bond to the inorganic material or 2) chosen on the basis that it is covalently bound to the inorganic material, the polymer may be infiltrated into the porous material as an already formed polymer after which binding between the polymer and the inorganic material is induced.

Similarly, composites can be produced with one or the other type of bonding but instead of infiltrating the formed polymers into the inorganic material, the monomers may be first infiltrated, then polymerized. The example described above with the resin monomer (involving ionic bonding) is the case where the monomer is infiltrated and then chemically cured using the free radical polymerization. In this case of the ionic bonding system the monomers are only curing (i.e. forming covalent bonds) with themselves to form the polymer chains. The pendant ionic groups on the monomers will form the ionic bonds on their own with the ionic groups of the porous matrix, possibly even before or at the same time that the free radical (curing) polymerization or monomers is occurring (via the vinyl groups). In the case of the covalent bonding system, curing will involve the pendant vinyl groups that have been coupled to the porous matrix with silanizing agents. Here, that reaction will form part of the curing process.

A partially polymerized organic polymer material with sufficiently low viscosity could also be infiltrated into the porous inorganic material and bonded.

While the above example used chemical curing of the monomer resin, it will be appreciated by those skilled in the art that any other curing technique may be used, for example, UV or visible light curing of the monomers or other energy sources of activation.

The composite materials may be produced for a wide variety of applications ranging from biomedical implants to stronger structural elements in non-biomedical applications. For biomedical applications they may be produced with materials to be biodegradable and/or bioresorbable in which the structure degrades or comes apart by a biodegradation process. The degraded parts may or may not be metabolically resorbed by the host body. Materials that are resorbed are biodegraded and eliminated and therefore are considered physiologically compatible.

While not wishing to be bound by any theory it is believed that the increased mechanical strength is due to the effect of strong primary chemical bonds (ionic or covalent) formed between the polymer and the ceramic material that serve to couple these two phases effectively and thereby allow effective stress transfer from one phase to the other. The organic polymer phase is relatively compliant and characterized by a low elastic modulus typical of organic polymeric materials (Young's Modulus, E ~0.1 to 1 GPa) while the CPP has a higher E (~50 GPa in its full density form) and like most inorganics is brittle and susceptible to crack initiation at stress concentration regions. The sinter necks present zones of high stress concentration and, therefore, are regions where cracks would be expected to initiate and then rapidly propagate through monolithic porous CPP samples. The addition of a well-bonded, efficient stress-transferring interface between the brittle CPP and compliant organic polymer (e.g. PVA-C resin) results in the dissipation of stress from these regions of stress concentration thereby lowering local stresses and inhibiting crack initiation. This results in a higher fracture strength and tougher material. The extension of this method of toughening to other combinations of ceramic and organic polymer is obvious provided that the necessary conditions of good bonding, good wetting (so all the free pore surfaces form ceramic-polymer bonds), and a sufficiently large difference in elastic constant between the ceramic and polymer phase exists. Other factors that may affect the magnitude of the property enhancement are the ratio of ceramic-to-polymer (see FIG. 13) and possibly the size of the pores into which the polymer phase intrudes.

The inventors also contemplate that it should be possible to form the open-pored ceramic structures by other methods such as laser ablation or drilling or diamond drilling or solid free form fabrication methods. Examples of organic phases that may be used to infiltrate such porous ceramic or glass structures are polycarbonate-based phosphate polymer resins, polycarbonate-based ammonium polymer resins; polycarbonate-based sulfonate polymer resins; polyester-based phosphate polymer resins; polysulfate phosphate polymer resins, polyurea phosphate polymer resins, polyamide phosphate polymer resins, polyalkylene oxide phosphate polymer resins, polylactone phosphate polymer resins, polyethersulfone phosphate polymer resins, polyvinyl phosphate polymer resins, polypeptide phosphate polymer resins; polysaccharide phosphate polymer resins; polyurethane phosphate polymer resins; polyethylene phosphate polymer resins, polypropylene phosphate polymer resins, polystyrene phosphate polymer resins, polysilicone phosphate polymer resins, poly (acrylonitrile-butadienestyrene) phosphate polymer resins, polybutadiene phosphate polymer resins, polyisoprene, polymethylmethacrylate phosphate polymer resins, polyvinylacetate phosphate polymer resins, polyacrylonitrile phosphate polymer resins, polyvinyl cloride phosphate polymer resins, polyethylene terephtahate phosphate polymer resins, cellulose and other polysaccharides phosphate polymer resins, polypeptide (glycine/glycine/arginine/glycine/aspartic acid) derivatized polycarbonate urethane phosphate polymer resins, polysaccharide (heparin) derivatized polycarbonate urethane phosphate polymer resins, polysaccharide (hyaluronic acid) derivatized polycarbonate urethane phosphate polymer resins and any other organic polymers that can form strong ionic bonds with the ceramic or glass surface. The key is that the organic phase is able to form a strong primary chemical bond (ionic or covalent) with the ceramic once it is infiltrated into the porous structure.

Summarizing, the present invention also provides novel composite materials based on porous ceramic materials infiltrated with polymers that can form ionic bonds to the ceramic material once infiltrated into the porous ceramic. The inventors have unexpectedly discovered that the mechanical strength of porous ceramic materials can be significantly increased by infiltrating those polymers into the porous ceramic material that are capable of forming strong primary bonds with the ceramic material.

FIGS. 12 and 13 show structural features (FIG. 12) and mechanical properties (FIG. 13) of an example of a novel composite material with ceramic material and a polymer which ionically bonds to it and results in a significant increase in mechanical properties. It will be understood that this example is non-limiting and is meant to be exemplary only so that the principle applies very broadly as a method of increasing the mechanical strength of porous inorganic (ceramic) materials.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

The invention claimed is:

1. A method for forming an inorganic material into three dimensional structures, comprising the steps of:
   a) forming an amorphous inorganic powder material having a melting temperature, a crystallization temperature, a glass transition temperature and a glass softening temperature;
   b) packing the formed amorphous inorganic powder material to produce a packed amorphous inorganic powder;
   c) pre-sintering the packed amorphous inorganic powder by heating said powder to a temperature greater than the glass transition temperature and the glass softening temperature and less than the crystallization temperature and holding steady at said temperature for an appropriate period of time to produce a pre-sintered amorphous inorganic body; and
   d) annealing the pre-sintered amorphous inorganic body to a final sintering temperature above the crystallization temperature and below the melting temperature to form a three dimensional porous crystalline inorganic structure.

2. The method according to claim 1 wherein the amorphous inorganic powder material is amorphous calcium polyphosphate powder having particles in a pre-selected particle size range.

3. The method as claimed in claim 2 wherein the pre-sintering temperature of the packed calcium polyphosphate is at between 570 and 600° C.

4. The method as claimed in claim 3 wherein the packed calcium polyphosphate is heated to generally 500° C. at a rate of generally 10° C. per minute, and heated to between 570 and 600° C. at a rate of 5° C. per minute, held at said temperature of between 570 and 600° C. for generally one hour and then heated to and held a the maximum final sintering temperature for generally one hour.

5. The method as claimed in claim 4 wherein the final sintering temperature of the pre-sintered calcium polyphosphate is at a temperature of generally between 585 and 950° C.

6. The method as claimed in claim 3 wherein the final sintering of the pre-sintered calcium polyphosphate is to a temperature of generally between 585 and 950° C.

7. The method as claimed in claim 2 wherein the final sintering of the pre-sintered calcium polyphosphate is at a temperature of generally between 585 and 950° C.

8. The method as claimed in claim 2 wherein the powder is packed to a packing density of generally 55%.

9. The method as claimed in claim 2 wherein the calcium polyphosphate powder has a predetermined maximum molecular chain length.

10. The method as claimed in claim 9 wherein the powder is producing by calcining calcium phosphate monobasic monohydrate to form a powder and melting the powder and maintaining the powder in a melted state between one and two hours, quenching the melted powders, and grinding the quenched melted powders to a predetermined size.

11. The method as claimed in claim 2 wherein the packed calcium polyphosphate powder is annealed in one of a ceramic and metallic mould to form a pre-sintered shape and the pre-sintered calcium polyphosphate body is removed from the mould and placed on one of a plate and foil of a non reactive, precious metal during the annealing.

12. The method as claimed in claim 2 wherein the calcium polyphosphate powder is packed and annealed in a non-reactive platinum or Pt-Rh mould to the final sintering temperature.

13. The method as claimed in claim 2 wherein the calcium polyphosphate powder further includes trace amounts of metallic element dopants.

14. The method as claimed in claim 13 wherein the metallic element is selected from the group consisting of titanium, magnesium, zirconium, iron, aluminum, cobalt, tantalum, silicon, nickel, copper, potassium and sodium.

15. The method as claimed in claim 1 wherein the amorphous inorganic powder material formed in step a) includes forming the amorphous inorganic powder material doped with an effective dopant for altering a rate of crystallization of the amorphous inorganic powder material.

16. The method as claimed in claim 15 wherein the dopants are one or more metallic elements.

17. The method as claimed in claim 16 wherein the metallic element is selected from the group consisting of titanium, magnesium, zirconium, iron, aluminum, cobalt, tantalum, silicon, nickel, copper, potassium and sodium.

18. A method as claimed in claim 17 wherein the metallic dopant is present as an ion and is selected from the group consisting of cations $Na^+$, $K^+$, $Ti^{4+}$, $Mg^{2+}$, $Zr^{2+}$, $Fe^{2+}$, $Fe^{3+}$, $Al^{3+}$, $Co^+$, $Ta^{5+}$, $Ni^{2+}$, $Cu^{1+}$, $Cu^{2+}$ and $Si^{4+}$.

19. The method as claimed in claim 2 wherein the amorphous calcium polyphosphate powder material formed in step a) includes forming the amorphous calcium polyphosphate powder doped with a pre-selected amount of an effective dopant for altering the processing conditions and/or the final chemical or physical properties of the formed porous calcium polyphosphate.

20. The method as claimed in claim 19 wherein at least one of the processing conditions which is altered by the presence of the effective dopant is a rate of crystallization of the amorphous inorganic powder material.

21. The method as claimed in claim 19 wherein the dopants are one or more metallic elements.

22. The method as claimed in claim 21 wherein the metallic element is selected from the group consisting of titanium, magnesium, zirconium, iron, aluminum, cobalt, tantalum, silicon, nickel, copper, potassium and sodium.

23. A method as claimed in claim 22 wherein the metallic dopant is present as an ion and is selected from the group consisting of $Na^+$, $K^+$, $Ti^{4+}$, $Mg^{2+}$, $Zr^{2+}$, $Fe^{2+ \: or \: 3+}$, $Al^{3+}$, $Co^+$, $Ta^{5+}$, $Ni^{2+}$, $Cu^{1+ \: or \: 2+}$ and $Si^{4+}$.

24. The method as claimed in claim 23 wherein the cations of $Na^+$, $K^+$, $Ti^{4+}$, and $Mg^{2+}$ are present in oxides $Na_2O$, $K_2O$, $TiO_2$ and $MgO$ respectively which are mixed into a calcium phosphate monobasic monohydrate powder used in step a) to produce the amorphous calcium polyphosphate powder material.

25. The method as claimed in claim 2 including controlling a relative humidity (RH) during application of the sintering procedure for controlling a temperature at which the amorphous calcium polyphosphate crystallizes.

26. The method as claimed in claim 25 wherein in step a) the amorphous inorganic powder material are formed having a particle size of between about 45 to about 250 μm, and wherein the packed amorphous calcium polyphosphate powder is pre-sintered by increasing the temperature at about 10° C./min to about 500° C. and then 5° C./min to about 585° C. and holding at about 585° C. for about 1 hour under conditions of Relative Humidity in a range from about 30 to 40%, and then sintering by increasing the temperature at about 10° C./min to between 700 and 950° C. and holding at this temperature for about 1 hour, then cooling to room temperature.

27. A method for forming a three dimensional porous crystalline inorganic structure, comprising the steps of:
   a) forming an amorphous inorganic powder material having a melting temperature, a crystallization temperature, a glass transition temperature and a glass softening temperature;
   b) packing the formed amorphous inorganic powder material to produce a packed amorphous inorganic powder;
   c) mixing fine powder particles of the amorphous inorganic powder material with a fluid carrier, and immersing the packed amorphous inorganic powder in the fluid carrier which has been mixed with the fine powder particles of the amorphous inorganic powder material to allow the fine powder particles to be distributed throughout the pores and on the surface of the packed amorphous inorganic powder following evaporation of the fluid carrier;
   d) pre-sintering the packed amorphous inorganic powder with the fine powder particles distributed therethrough at a pre-sintering temperature which is above the glass softening and the glass transition temperature but sufficiently low and for a short enough period of time to prevent the crystallization of the fine powder particles but to bond the fine powder particles to the packed amorphous inorganic powder; and
   e) annealing the pre-sintered packed amorphous inorganic powder to a final sintering temperature above the crystallization temperature and below the melting temperature to form a three dimensional porous crystalline inorganic structure.

28. The method according to claim 27 wherein the amorphous inorganic powder material is amorphous calcium polyphosphate powder, and wherein the fine powder particles of the amorphous inorganic powder material are fine calcium polyphosphate powder having a mean diameter less than about 50 μm to give a composite of crystalline and amorphous three dimensional porous calcium polyphosphate structure with regions that will degrade much more rapidly in vivo thereby releasing $Ca^{2+}$ and $PO_4^{3-}$ at faster rates from these regions while still retaining the initial integral porous calcium polyphosphate structure.

29. The method according to claim 28 wherein the fluid carrier has a sufficiently low viscosity to be able to infiltrate into the porous calcium polyphosphate structure while not readily dissolving the calcium polyphosphate that can be removed by heating without leaving a residue that is not biocompatible.

30. The method according to claim 29 wherein the fluid carrier is selected from the group consisting of water and alcohols.

31. The method as claimed in claim 1 further including a step of infiltrating the formed three dimensional porous crystalline inorganic structure with an organic polymer, or monomers of the polymer, which is able to form strong primary chemical bonds with the porous, inorganic ceramic material to form a composite ceramic/polymer material.

32. The method as claimed in claim 2 further including the step of infiltrating the formed porous crystalline calcium polyphosphate structure with an organic polymer, or monomers of the polymer, the polymer being able to form strong primary chemical bonds between the polymer and the porous crystalline calcium polyphosphate.

33. The method according to claim 31 wherein the monomers are infiltrated into the three dimensional porous crystalline inorganic structure and thereafter polymerized to the polymer.

34. The method according to claim 33 wherein the monomers are polymerized by one of heat induced curing, free radical polymerization and light induced curing.

35. The method according to claim 31 wherein the organic polymer is selected so that it covalently binds to the three dimensional porous crystalline inorganic structure.

36. The method according to claim 31 wherein the organic polymer is selected so that it ionically binds to the three dimensional porous crystalline inorganic structure.

37. The method according to claim 32 wherein the monomers are infiltrated into the porous crystalline calcium polyphosphate structure and thereafter polymerized to the polymer.

38. The method according to claim 32 wherein the organic polymer is selected so that it covalently binds to the three dimensional porous crystalline inorganic structure.

39. The method according to claim 32 wherein the organic polymer is selected so that it ionically binds to the three dimensional porous crystalline inorganic structure.

40. The method according to claim 32 wherein the composite material is biodegradable.

41. The method according to claim 32 wherein the composite material is biodegradable and resorbable.

42. The method as claimed in claim 32 including machining the resulting composite material to a desired shape and form while retaining suitable mechanical strength and fracture resistance as a result of the good damage tolerance of the interpenetrating phase composite thereby minimizing microcrack formation and growth during machining.

43. The method as claimed in claim 27 wherein in step a) the amorphous inorganic powder material are formed having a particle size of between about 150 to about 250 µm, and wherein the fine powder particles of the amorphous inorganic powder material have a particle size less than 44 µm.

* * * * *